United States Patent
Kaplan

(10) Patent No.: US 8,802,734 B2
(45) Date of Patent: *Aug. 12, 2014

(54) METHOD OF TREATING OR PREVENTING PAIN

(75) Inventor: Eliahu Kaplan, Petah Tiqwa (IL)

(73) Assignee: Novaremed Limited (IL)

( * ) Notice: Subject to any disclaimer, the term of this patent is extended or adjusted under 35 U.S.C. 154(b) by 500 days.

This patent is subject to a terminal disclaimer.

(21) Appl. No.: 12/878,522

(22) Filed: Sep. 9, 2010

(65) Prior Publication Data

US 2011/0086910 A1    Apr. 14, 2011

Related U.S. Application Data

(60) Provisional application No. 61/240,841, filed on Sep. 9, 2009.

(51) Int. Cl.
| | | |
|---|---|---|
| *A01N 37/18* | (2006.01) | |
| *A61K 31/165* | (2006.01) | |
| *A01N 33/18* | (2006.01) | |
| *A01N 33/24* | (2006.01) | |
| *A61K 31/045* | (2006.01) | |
| *A01N 31/08* | (2006.01) | |
| *A61K 31/05* | (2006.01) | |

(52) U.S. Cl.
CPC .................................. *A61K 31/165* (2013.01)
USPC ............................ 514/617; 514/728; 514/731

(58) Field of Classification Search
None
See application file for complete search history.

(56) References Cited

U.S. PATENT DOCUMENTS

| | | | |
|---|---|---|---|
| 2,908,691 A | 10/1959 | Robinson | |
| 4,766,106 A | 8/1988 | Katre et al. | |
| 4,908,322 A | 3/1990 | Jacobson et al. | |
| 5,541,206 A | 7/1996 | Kempf et al. | |
| 5,585,397 A | 12/1996 | Tung et al. | |
| 7,642,290 B2 | 1/2010 | Kaplan | |
| 7,674,829 B2 | 3/2010 | Kaplan | |
| 8,252,843 B2* | 8/2012 | Kaplan | 514/649 |
| 8,309,606 B2* | 11/2012 | Kaplan | 514/538 |
| 2006/0135620 A1 | 6/2006 | Kaplan | |
| 2006/0148874 A1 | 7/2006 | Kaplan et al. | |
| 2009/0306214 A1 | 12/2009 | Kaplan | |

FOREIGN PATENT DOCUMENTS

| | | |
|---|---|---|
| CN | 101503370 A | 8/2009 |
| CN | 101503373 A | 8/2009 |
| EP | 0887340 A1 | 12/1998 |
| EP | 1876169 A1 | 1/2008 |
| GB | 1392674 A | 4/1975 |
| JP | 07101924 A | 4/1995 |
| WO | WO-9723202 A1 | 7/1997 |
| WO | WO-9729079 A1 | 8/1997 |
| WO | WO-0246176 A1 | 6/2002 |
| WO | WO-2004031129 A2 | 4/2004 |
| WO | WO-2005092305 A2 | 10/2005 |
| WO | WO-2007129226 A2 | 11/2007 |
| WO | WO-2009039218 A2 | 3/2009 |
| WO | WO-2009109850 A2 | 9/2009 |

OTHER PUBLICATIONS

Treede et al. (Neurology Apr. 29, 2008 vol. 70 No. 18 1630-1635) at abstract.*
Nicolaus, B.J.R., "Symbiotic Approach to Drug Design", *Decision Making in Drug Research*, pp. 173-186 (1983).
Adamczyk et al., "Stereoselective *Pseudomonas cepacia* lipase mediated synthesis of a-hydroxyamides", *Tetrahedron: Asymmetry*, 8(15):2509-2512 (1997).
Amara et al. "Circulating autoantibodies directed against conjugated fatty acids in sera of HIV-1-infected patients", *Clin. Exp. Immunol.*, 96:379-383 (1994).
Amat et al., "Sythesis of Enantiopure Trans-3,4-Disubstituted Piperidines. An Enantiodivergent Synthesis of (+)- and (−)-Paroxetine", *The Journal of Organic Chemistry*, 65(10):3074-3084 (2000), XP002468547 ISSN: 0022-3263.
Arutyunyan et al., "Synthesis of Pseudosparsomycins", *Pharm. Chem. J.*, (English Translation), 23(10):837-840 (1989).
Azzouz et al., "Selective Tetrahydropyranylation under Non-Acidic Conditions", *Synlett* Nov. 3, 2005 Germany, No. 18, 2808-2810 (2005), XP002468546 ISSN: 0936-5214.
Beaulieu et al, "2',6'-Dimethylphenoxyacetyl: A New Achiral High Affinity $P_3$-$P_2$ Ligand for Peptidomimetic-Based HIV Protease Inhibitors", *J. Med. Chem.*, 43(6):1094-1108 (2000).
Braun et al., "Darstellung von Aldehyden and Ketonen mit Hilfe des Abbaues quartdrer Ammoniumbasen", Chem. Ber., in German, 65(14):235-241 (1929).

(Continued)

*Primary Examiner* — James D Anderson
*Assistant Examiner* — William Lee
(74) *Attorney, Agent, or Firm* — Mintz Levin Cohn Ferris Glovsky and Popeo, P.C.; Shovon Ashraf

(57) ABSTRACT

Compounds for use in the treatment or prophylaxis of pain, including acute and chronic pain (e.g., nociceptive pain, neuropathic pain, headaches, migraine), represented by general formula I:

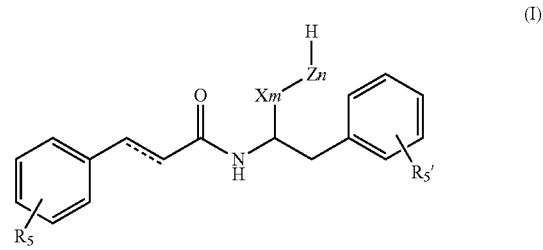

(I)

in which:
the dotted line represents a single or a double bond; and $R_5$ and $R_5'$ are independently —H, —OH or —$OR_6$, where $R_6$ is a linear or branched $C_1$-$C_4$ alkyl; X is —$CH_2O$—; Z is —$CH_2CH_2O$—, —$CH(CH_3)CH_2O$— or —$CH_2CH(CH_3)O$—; m is 1; and n is an integer of 1-5. The compounds of the invention are also effective for reducing inflammation and may be used alone or in combination with other analgesics.

20 Claims, 19 Drawing Sheets

(56) References Cited

OTHER PUBLICATIONS

Braun et al., "New Oxidative Transformations of Phenolic and Indolic Oxazolines: An Avenue to Useful Azaspirocyclic Building Blocks", *J. Org. Chem.*, 65(14):4397-4408 (2000).

Burke et al., "Hydroxylated Aromatic Inhibitors of HIV-1 Integrase", *J. Med. Chem.*, 38(21):4171-4178 (1995).

Burke, Jr. et al. "Small Hydroxylated Aromatic Inhibitors of HIV-1 Integrase as Potential Anti-AIDS Drugs", NM Conference on Retroviral Integrase Molecular and Pharmacology a Novel Target for the Treatment of AIDS, pp. 1-2, XP-000980354 (1995).

Bussolari et al., "Parallel synthesis of 2-alkoxy and 2-acyloxyphenylpropyl amides and amines using dihydrocoumarins as versatile synthons. Application of a novel resin quenchcapture method", *Tetrahedron Lett.*, 40(7):1241-1244 (1999).

Caldirola et al., "New prenylamine-analogues: investigations of their influence on calcium-dependent biological systems", *Eur. J. Med. Chem.*, 28:555-568 (1993).

Chemical Abstracts Service, JP 52 036606 A2, "Process for Preparation of Amino Compounds", Tanabe Seiyaku Co. Ltd. (Mar. 22, 1977).

Clark et al., "Some Substituted Phenethyl and 3-Phenylpropyl Styryl Ketones and the Corresponding Saturated Ketones", *J. Chem. Soc.*, pp. 126-130 (1962).

Davyt et al., "A new Indole Derivative from the Red *AlgaChondria atropurpurea*. Isolation, Structure Determination, and Anthelmintic Activity", *J. Nat. Prod.*, 61(12):1560-1563 (1998).

Detert et al., "Cationic amphiphiles with G-protein-stimulatory activity: Studies on the role of the basic domain in the activation process" *Pharmazie*, 51(2):67-72 (1996).

Dumont et al., "Note on Attempts to Prepare Ring-B Homomorphinan-6-ones by *Grewe* Cyclization from Octahydro-l-phenethylisoquinolines", *Helvetica Chimica Acta*, 68(8):2128-2131 (1985).

Glennon et al., "Influence of Amine Substituents on 5-HT2A versus 5-HT2C Binding of Phenylalkyl- and Indolylallcylamines",*J. Med. Chem.*, 37(13):1929-1935 (1994).

Greenfield et al., "Convenient Synthesis of Functionalized Terphenyls", *Tetrahedron Letters, Elsevier*, Amsterdam, NL, 44(13):2729-2732 (2003), XP004413304 ISSN: 0040-4039.

Greenwald et al., "Highly Water Soluble Taxol Derivatives: 7-Polyethylene Glycol Carbamates and Carbonates", *Journal of Organic Chemistry*, 60:331-336 (1995).

Heilbron et al., "CLXXVIL-Styrylpyrylium Salts. Part XIII. The Reactivity of Methyl P-Phenylethyl and Methyl 7-Phenylpropyl Ketones", *J. Chem. Soc.*, pp. 1336-1342 (1931).

Herbert et al., "The Biosynthesis of *Sceletium* Alkaloids in *Sceletium Subvelutinum* L. Bolus", *Tetrahedron*, 46(20):7105-7118 (1990).

Hochstein, "Quantitative Studies on Lithium Aluminum Hydride Reactions", *J. Am. Chem. Soc.*, 71:305-307 (1949).

Horii et al., "Syntheses and Pharmacological Properties of 2- and 3-Arallcyltetrahydro-1,3-oxazines", *Chem. Pharm. Bull.*, 13(10):1151-1159 (1965).

Kamenecka et al., "Construction of Substituted Cyclohexanones by Reductive Cyciization of 7oxo2,8-alkadienyl Esters", *Organic Lett.*, 4(1):79-82 (2002).

Karrer et al. *Helvetica Chimica Acta*, in German, 31:1617-1623 (1948).

Kunishima et al., "Synthesis and Characterization of 4(4,6-Dimethxy-1,3,5-triazin-2-yl)-4-methylmorpholinium Chloride", *Tetrahedron Lett.*, 40:5327-5330 (1999).

Külz et al., "Ober Synthesen spasmolytisch wirkender Stoffe. II. Mitteilung",Chem. Ber., in German, 72:2161-2166 (1939).

Le Blanc et al., "New Access to Spiranic p-Lactams", *Tetrahedron Lett.*, 33(15):1993-1996 (1992).

Lee et al., "Effects of Phenolic Acid Esters and Amides on Stimulus-Induced Reactive Oxygen Species Production in Human Neutrophils", *Clinica Chimica Acta*, 352(1-2):135-141 (2005).

Liang, "CXCR4, Inhibitors and Mechanisms of Action" *Chemical Biology & Drug Design*, 72:97-110 (2008).

Lin et al., "Anti-Inflammatory Neolignans from Piper Kadsura", *Journal of Natural Products*, 69(5):842-844 (2006), XP002468545 ISSN: 0163-3864.

Luly et al., "Modified Peptides which Display Potent and Specific Inhibitionof Human Renin", *Biochem. Biophys. Res. Commun.*, 143(1):44-51 (1987).

Marquez et al., "Anti-Inflammatory Evaluation and Phytochemical Characterization of Some Plants of the *Zanthoxylum* Genus", *Acta Farm. Bonarense*, 24(3):325-330 (2005).

Morisaki et al., "Synthesis of Novel Vitamin C Phosphodiesters: Stability and Antioxidant Activity", *Carbohydrate Research, Elsevier Scientific Publishing Company*, Amsterdam, NL, 286:123-138 (1996), XP004018659 ISSN: 0008-6215.

Nesterenko, Vitally et al., "Identification from a Combinatorial Library of a Small Molecule that Selectively Induces Apoptosis in Cancer Cells", *Journal of the American Chemical Society*, 125(48):14672-14673 (2003), XP002468543 ISSN: 0002-7863.

Nivlet et al., "Reductive Opening of Cyclopropylogous a-Hydroxy Aldehydes and Ketones by Samarium(II) Iodide", *Tetrahedron Lett.*, 39:2115-2118 (1998).

Obora et al., "Palladium Complex Catalyzed Acylation of Allylic Esters with Acylsilanes",./ *Am. Chem. Soc.*, 123(43):10489-10493 (2001).

Ochiai et al., "Triphenylphosphine-mediated olefmation of aldehydes with (Z)-(2-acetoxyalk-l-enyl)phenyl-$k^3$-iodanes", *Chem. Commun.*, 13:1157-1158 (2000).

Park et al., "N-Caffeoyltyramine Arrests Growth of U937 and Jurkat Cells by Inhibiting Protein Tyrosine Phosphorylation and Inducing Caspase-3", *Cancer Letters*, 202(2):161-171 (2003), XP002468544 ISSN: 0304-3835.

Park, "Caffedymine from Cocoa has COX Inhibitory Activity Suppressing the Expression of a Platelet Activation Marker, P-Selectin", *J Agric. Food Chem.*, 55(6):2171-2175 (2007).

Paul et al., "Condensation de quelques ethers vinyliques heterocycliques avec l'acroleine et ses homologues", *Bull. Soc. Chim. Fr.*, in French, pp. 672-678 (1954).

Rao et al., "Synthetic Studies in Polycyclic Systems: Part VP'—Syntheses of 3- Phenyl-, I-Methyl-3- phenyl- & 1,3-Diphenyl-phenanthrenes", *Ind. J. Chem.*, 14B:38-40 (1976).

Repke et al. "Synthesis of S(+) and R(−)-3-(2-Aminopropyl)indole from Ethyl-$_D$- and $_L$- Tryptophanate", *J. Heterocyclic Chem.*, 13:7775-7778 (1976).

Takeuchi et al., "Inhibitory effects of derivatives of tyrosine and tryptophan on mollusca giant neurons", *Neurosci.*, 9(1):122-123 (1983).

Takeuchi et al., Abstract of Comparative Biochemistry and Physiology, C: Comparative Pharmacology (1983) 75C(2), 329-335.

Tamiz et al., "Structure-Activity Relationships for a Series of Bis(phenylalkyl)amines: Potent Subtype Selective Inhibitors of N-Methyl-D-aspartate Receptors", *J. Med. Chem.*, 41(18):3499-3506 (1998).

Umino et al., "Sodium Acyloxyborohydride as New Reducing Agents. I. Reduction of Carboxamides to the corresponding Amines", *Tetrahedron Lett.*, No. 10, pp. 763-766 (1976).

Yasuma et al., "Synthesis of Peptide Aledehyde Derivatives as Selective Inhibitors of Human Cathepsin L and their Inhibitory Effect on Bone Resorption", *J. Med. Chem.*, 41(22):4301-4308 (1998).

Zhao et al., "Arylamide Inhibitors of HIV-1 Integrase", *J. Med. Chem.*, 40:1186-1194 (1997).

Richeimer. "The Richeimer Pain Update." Dec. 2000. Web. Aug. 24, 2013. http://www.helpforpain.com/arch2000dec.htm.

* cited by examiner

METHOD OF TREATING OR PREVENTING PAIN

RELATED APPLICATION

This application claims priority under 35 U.S.C. §119(e) to U.S. provisional application Ser. No. 61/240,841, filed Sep. 9, 2009 which is incorporated herein by reference.

BACKGROUND

The present invention relates to the treatment or prophylaxis of pain and provides a method of treating or preventing pain as well as the use of certain compounds in the manufacture of medicaments for the treatment or prophylaxis of pain in humans and non-human animals. Pain is a multifaceted or multidimensional, experiential response to a variety of stimulus conditions. Pain is defined by the International Association for the Study of Pain (IASP) as "an unpleasant sensory and emotional experience associated with actual or potential tissue damage, or described in terms of such damage".

Pain in animals is frequently the result of nociception, i.e., activity in the nervous system that results from the stimulation of nociceptors. Neuropathic pain differs from nociceptive pain in that it involves damage to the nerve resulting in the sensation of pain. In central pain, the pain is generated in the brain from some form of lesion. Occasionally pain may be psychogenic, i.e., caused by mental illness.

Pain can be acute or chronic. Acute pain is usually caused by soft tissue damage, infection and/or inflammation among other causes. Acute pain serves to alert after an injury or malfunction of the body. Chronic pain may have no apparent cause or may be caused by a developing illness or imbalance. Chronic pain is defined as the disease of pain; its origin, duration, intensity and specific symptoms may vary.

The experience of physiological pain can be grouped according to the source and related nociceptors. Cutaneous pain is caused by injury to the skin or superficial tissues. Cutaneous nociceptors terminate just below the skin, and due to the high concentration of nerve endings, produce a well-defined, localised pain of short duration. Examples of injuries that produce cutaneous pain include paper cuts, minor cuts, minor (first-degree) burns and lacerations. Somatic pain originates from ligaments, tendons, bones, blood vessels and nerves. It is detected with somatic nociceptors. The scarcity of pain receptors in these areas produces a dull, poorly-localised pain of longer duration than cutaneous pain; examples include sprains and broken bones. Myofascial pain is usually caused by trigger points in muscles, tendons and fascia and may be local or referred. Visceral pain originates from the body's viscera or organs. Visceral nociceptors are located within body organs and internal cavities. The even greater scarcity of nociceptors in these areas produces pain that is usually more aching and for longer duration than somatic pain. Visceral pain is extremely difficult to localise, and several injuries to visceral tissue exhibit "referred" pain, where the sensation is localised to an area completely unrelated to the site of injury. Phantom limb pain, a type of referred pain, is the sensation of pain from a limb that has been lost or for which a person no longer receives physical signals. Neuropathic pain may occur as a result of injury or disease to the nerve tissue itself. This can disrupt the ability of the sensory nerves to transmit correct information to the thalamus, and hence the brain interprets painful stimuli even though there is no obvious unknown psychological cause for the pain.

Acute pain is usually treated simultaneously with pharmaceuticals or appropriate techniques for removing the cause and pharmaceuticals or appropriate techniques for controlling the pain sensation, commonly analgesics.

Analgesics fall into three categories: opioid (narcotic) analgesics, non-opioid analgesics and adjuvant analgesics. Opioid analgesics are powerful analgesics that are chemically related to morphine. However, opioids have many side effects, which may be more likely to occur in people with certain disorders: kidney failure, a liver disorder, chronic obstructive pulmonary disease (COPD), dementia or another brain disorder. Drowsiness, constipation, nausea, vomiting and itching are common when opioids are started. Apart from morphine, opioid analgesics known at the time of writing include codeine, fentanyl, hydrocodone, hydromorphone, levorphanol, meperidine, methadone, oxycodone, oxymorphone, pentazocine and propoxyphene.

A variety of non-opioid analgesics are also available at the time of writing. They are often effective for mild to moderate pain. Most non-opioid analgesics are classified as non-steroidal anti-inflammatory drugs (NSAIDs). An example of an analgesic that is not an NSAID is acetaminophen, which is commonly known as paracetamol. Acetaminophen has substantially no anti-inflammatory properties.

NSAIDs are used to treat mild to moderate pain and may be combined with opioids to treat moderate to severe pain. NSAIDs not only relieve pain, but they also reduce the inflammation that often accompanies and worsens pain. Although widely used, NSAIDs can also have side effects, sometimes serious ones, including problems in the digestive tract, bleeding problems, problems related to retaining fluids and increased risk of heart and blood vessel disorders. Current NSAIDs include aspirin, ibuprofen, ketoprofen, naproxen, cox-2 inhibitors such as celecoxib, choline magnesium trisalicylate, diflunisal, salsalate, diclofenac, etodolac, fenoprofen, flurbiprofen, indomethacin, ketorolac, meclofenamate, mefenamic acid, meloxicam, nabumetone, oxaprozin, piroxicam, sulindac and tolmetin.

Adjuvant analgesics include antidepressants such, for example, as imipramine, amitriptyline, bupropion, desipramine, fluoxetine and venlafaxine; anticonvulsants (such as carbamazepine, gabapentin and pregabalin) and oral and topical local anaesthetics.

In the treatment of chronic pain, the "Three-Step Analgesic Ladder" developed by the World Health Organization is often used. For mild pain, acetaminophen, aspirin or other NSAIDs may be employed. For mild to moderate pain, week opioids such as codeine and dihydrocodeine are employed in combination with acetaminophen, aspirin or other NSAIDs. In the case of moderate to severe pain, strong opioids such as morphine, diamorphine, or fentanyl, hydromorphone, methadone, oxycodone or phenazocine may be administered in combination with acetaminophen, aspirin or other NSAIDs.

SUMMARY OF THE INVENTION

An object to the present invention is to provide alternative compounds for the treatment or prophylaxis of pain. In particular, it is object to the present invention to provide alternative NSAIDs for the treatment or prophylaxis of pain and to reduce inflammation. Desirably the compounds of the invention should have no or substantially no adverse activity on the central nervous system.

Another object of the present invention is to provide an alternative method for the treatment or prevention of pain.

According to one aspect of the present invention therefore there are provided compounds for use in the treatment or prevention of pain, which compounds may be represented by general formula I below:

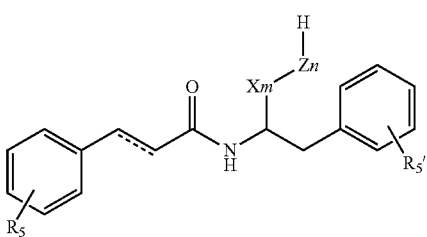

(I)

in which:
⁓⁓⁓ represents a single or a double bond; and $R_5$ and $R_5'$ are independently —H, —OH or —$OR_6$, where $R_6$ is a linear or branched $C_1$-$C_4$ alkyl;
X is —$CH_2O$—,
Z is —$CH_2CH_2O$—, —$CH(CH_3)CH_2O$— or —$CH_2CH(CH_3)O$—; m is 1; and n is an integer of 1-5, preferably n is 1 or 2.

Suitably, said compounds may be the S-enantiomers of the compounds represented by formula I above. The invention also comprehends the use of the respective pharmaceutically acceptable salts, prodrugs, metabolites, and hydrates of the compounds of formula I.

The compounds of the present invention may be used for the treatment or prophylaxis of acute or chronic pain. For instance, the compounds may be used for the treatment of nociceptive pain such, for example, as cutaneous pain, somatic pain, myofascial pain, visceral pain, phantom limb pain or neuropathic pain. The compounds of the invention may also be used treatment of headaches or migraine. The compounds may be used alone or in combination with acetaminophen or another NSAID for the treatment of mild chronic pain or in conjunction with weak or strong opioids for the treatment of moderate or severe pain.

The compounds of the invention may also be employed in the treatment or prophylaxis of neuropathic pain and may be used in conjunction with one or more antidepressants or antiepileptic medicaments such, for example, as gabapentin or pregabalin.

According to another aspect of the present invention therefore there is provided a method for treating or preventing pain in a human or non-human animal patient, which method comprises administering to said patient in need thereof a therapeutic effective amount of one or more of the compounds of the invention.

For a human patient, a daily dose of 1.0 mg to 15 g of said one or more compounds in a pure, substantially pure or partially pure form as described in more detail below may suitably be administered. The compounds may be administered under the supervision of a medical practitioner in an amount sufficient to achieve effective pain management. In some embodiments, the daily dose of said one or more compounds may be titrated to determine such effective amount. Said daily dose may comprise about 5.0 mg to 1 g, typically about 5 mg to 500 mg. In some embodiments, said dose may comprise 10 mg to 100 mg per day of said one or more compounds. The compounds may be administered on a regimen of one to four times per day.

Said one or more compounds may be administered parenterally, transdermally, intramuscularly, intravenously, intradermally, intranasally, subcutaneously, intraperitoneally, intraventricularly or rectally. Preferably, the one or more compounds are administered orally. Optionally, the one or more compounds of the present invention may be administered simultaneously, sequentially or separately with at least one opioid analgesic, an antidepressant or an antiepileptic medicament. Alternatively, the one or more compounds of the invention may be administered simultaneously, sequentially or separately with one or more other NSAIDs or acetaminophen.

In yet another aspect of the present invention there is provided the use of one or more of the compounds of the invention in the manufacture of a medicament for use in the treatment or prophylaxis of pain. Said medicament may be manufactured for co-administration with one or more of acetaminophen, another NSAID, an opioid, an antiepileptic or an antidepressant. Advantageously, it has been found that the compounds of the present invention are effective for reducing or preventing inflammation. It has also been found that the compounds of the invention have no or substantially no (i.e., within acceptable limits) deleterious effect on the central nervous system.

As mentioned above, n may be 1, 2, 3, 4, or 5, preferably 1 to 2.

In some embodiments of the invention, the compounds of the invention may be represented by general formula II below:

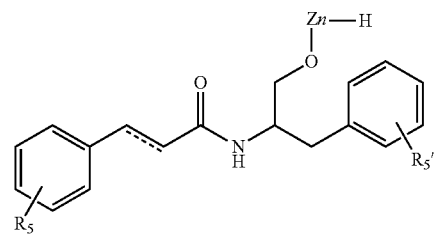

(II)

in which ⁓⁓⁓ , n, Z, $R_5$ and $R_5'$ are as defined above.
Z may be —$CH_2CH(CH_3)O$—.
Z may be —$CH(CH_3)CH_2O$—.

In some embodiments of the present invention, the compounds of the invention may therefore be represented by general formula III below:

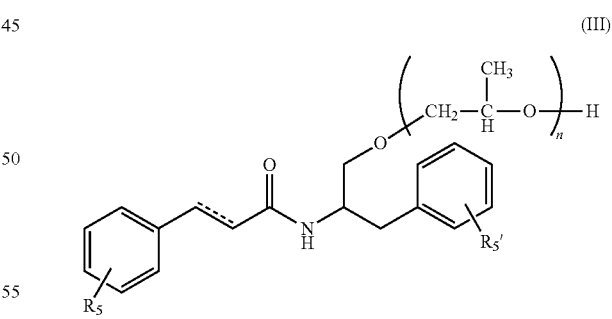

(III)

in which n, $R_5$ and $R_5'$ are as defined above.
$R_5$ may be H. Alternatively, $R_5$ may be OH.
$R_5'$ may be H. Alternatively, $R_5'$ may be OH.

Suitably, n may be an integer from 1-5, preferably 1-3, more preferably 1-2. For example, n may be 1, 2, 3, 4 or 5. Advantageously, n may be 1-2, e.g., 1.

Alternatively, the compounds of the invention may be the S-enantiomers of the compounds represented by general formulae IV, V, VI and VII below:

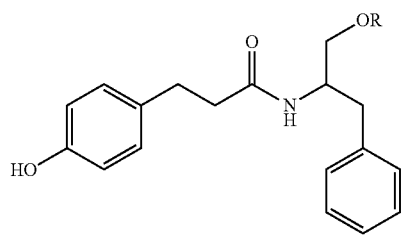
(IV)

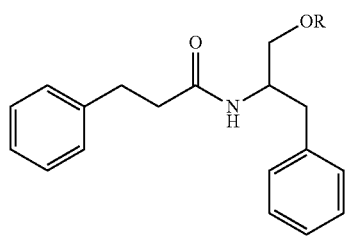
(V)

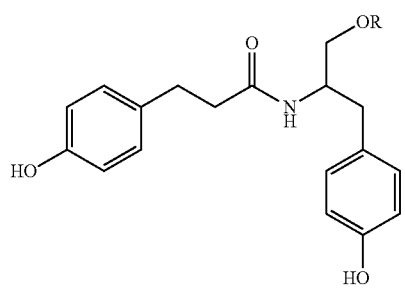
(VI)

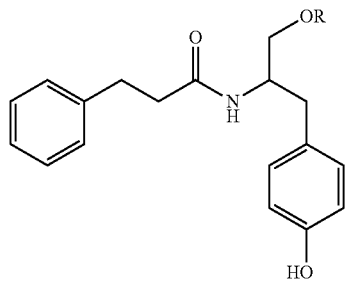
(VII)

in which R is a polyalkylene glycol polymer having n units, wherein n is as defined above, particularly n=1, 2, 3, 4, or 5.

Suitably, said polyalkylene glycol polymer may be polyisopropylene glycol.

In a preferred aspect, the compounds of the invention are a compound of formula VII, more preferably a compound having one of the following formulas.

Compound 1

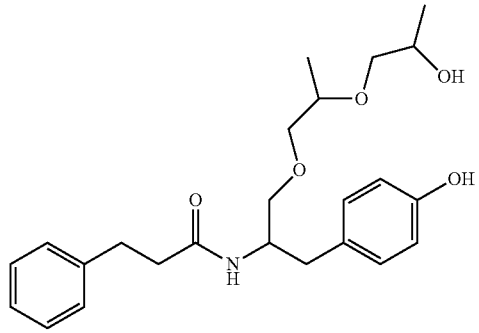

(NRD 71)

Compound 2

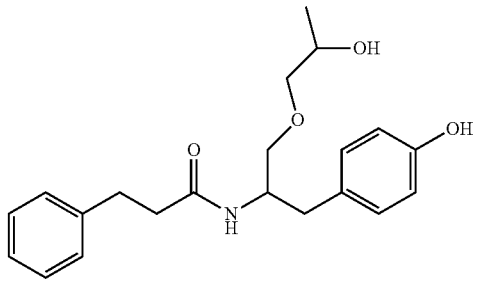

(NRD 135)

Compound 3

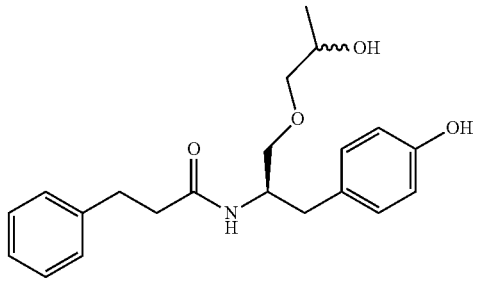

(NRD 175)

All chiral, diastereomeric, racemic, and geometric isomeric forms of a structure are intended, unless specific stereochemistry or isomeric form is specifically indicated. For example, for compound 2, the following isomeric forms are intended:

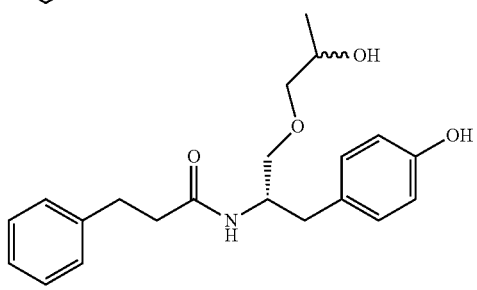

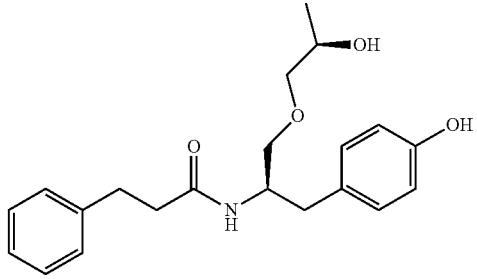

7
-continued
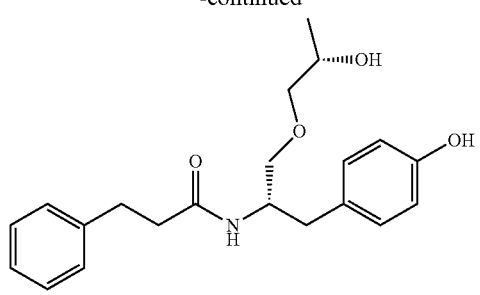
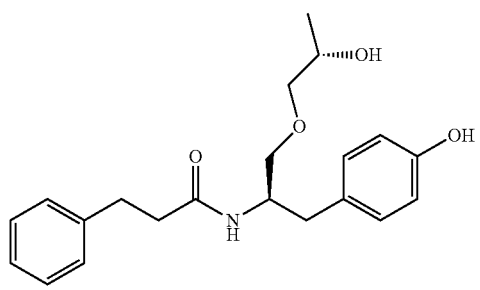
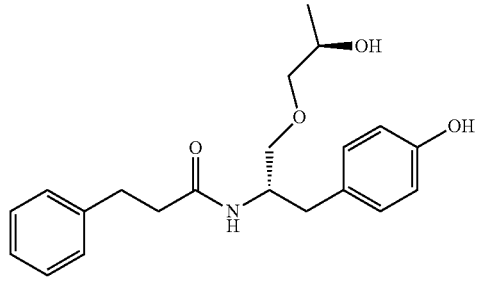
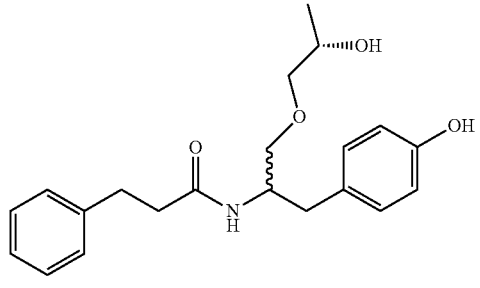
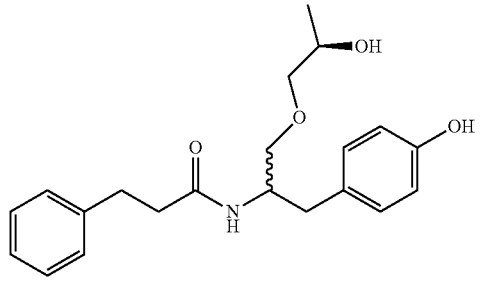
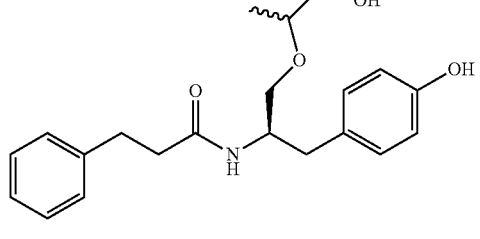
8
-continued
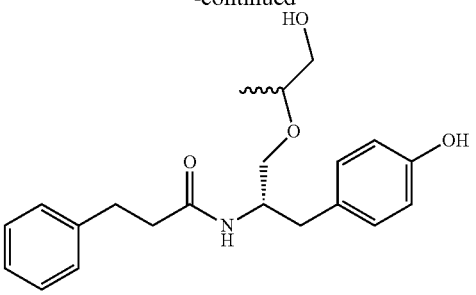
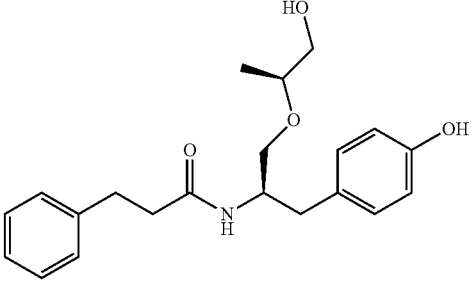
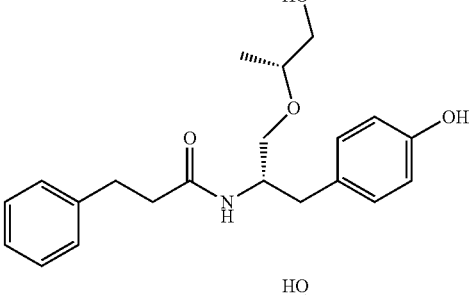
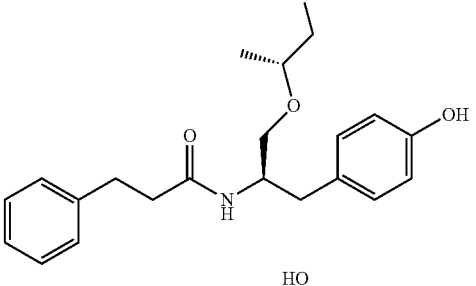
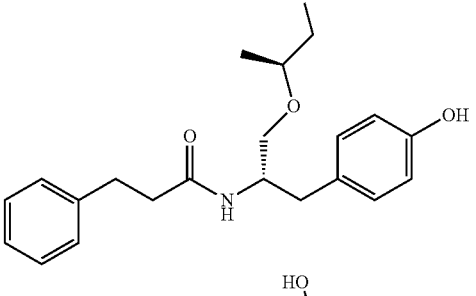
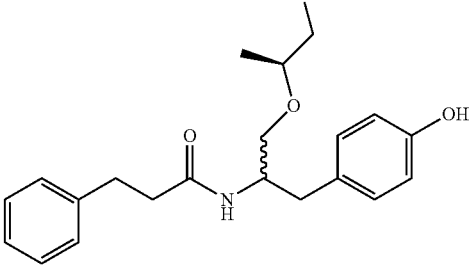

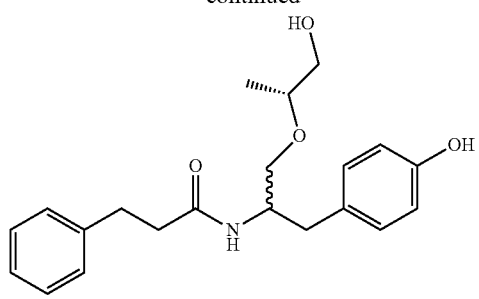
For example, some isomeric forms of compound 1 are shown below:
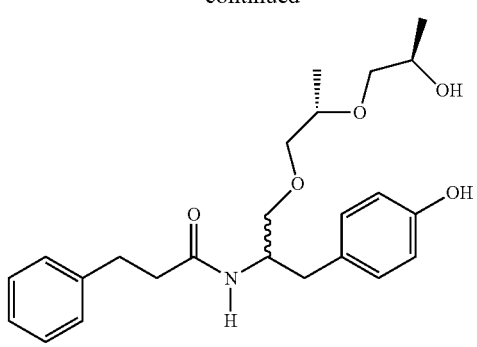
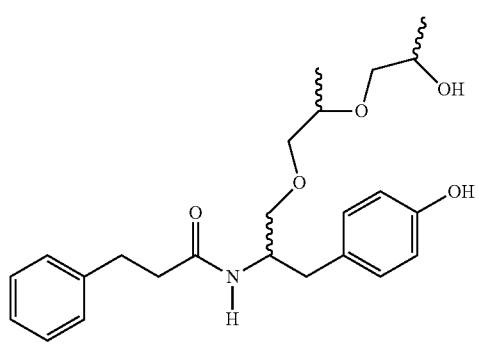
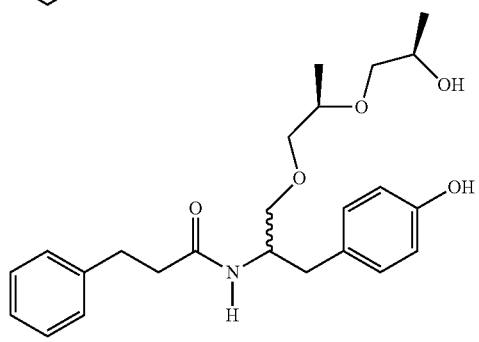
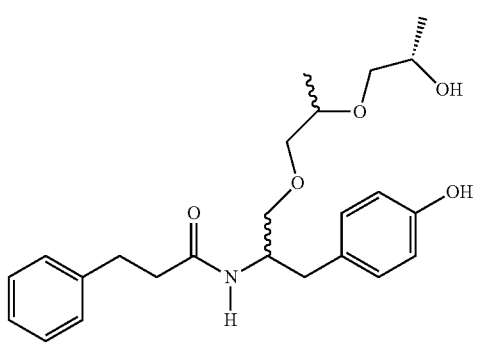
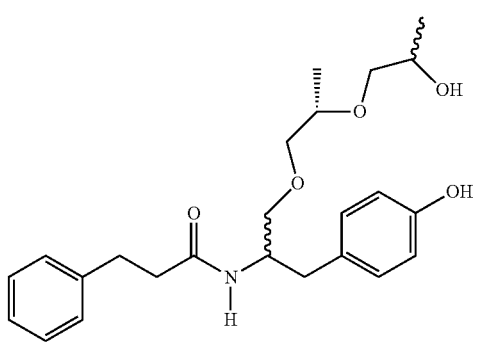
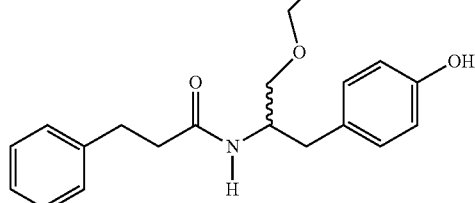
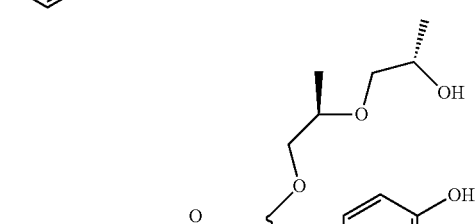
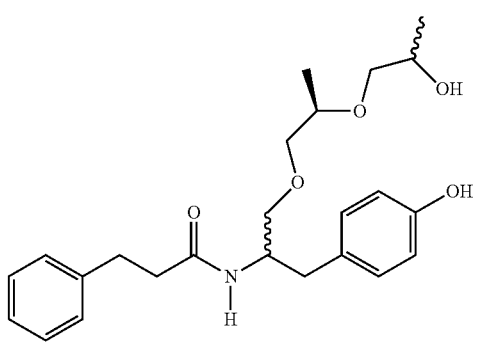
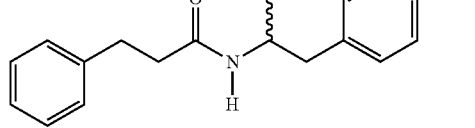

11
-continued
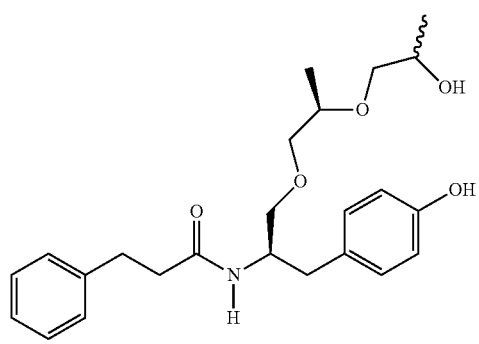
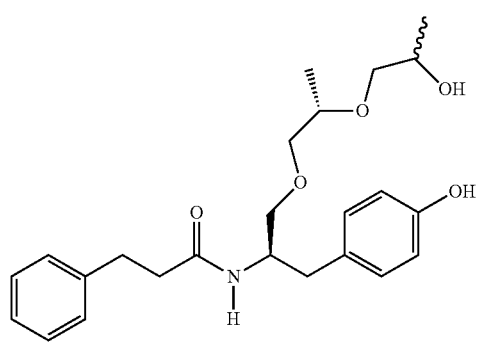
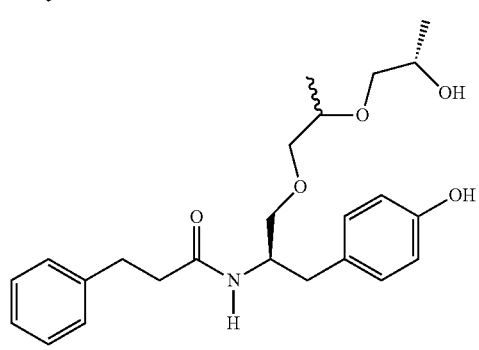
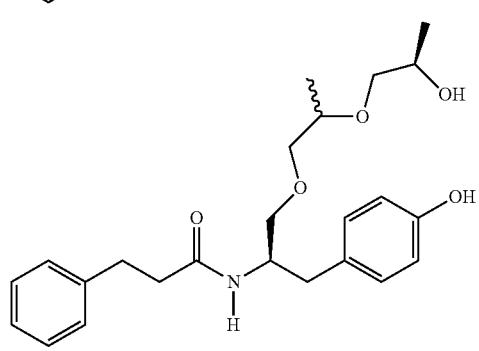
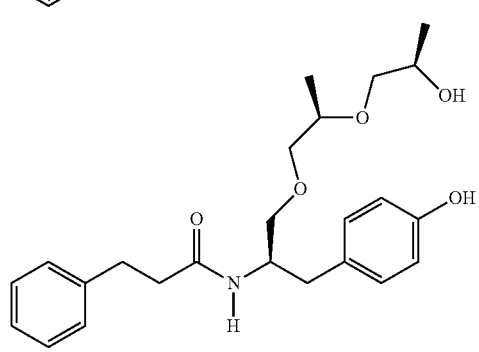
12
-continued
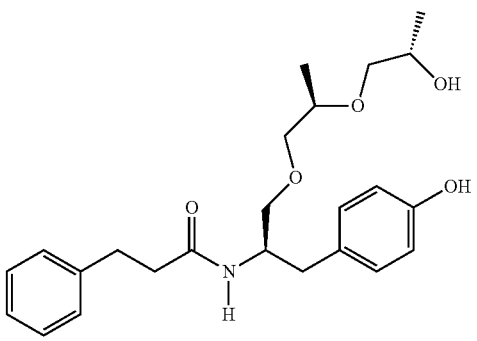
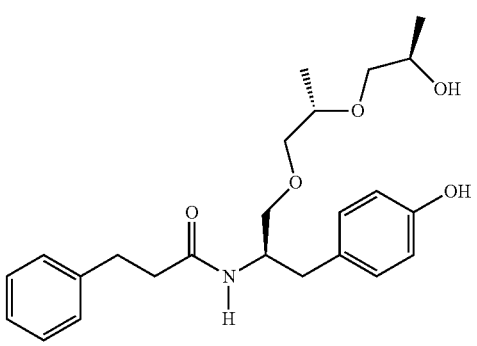
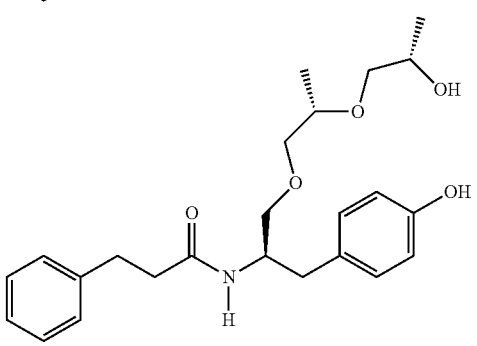
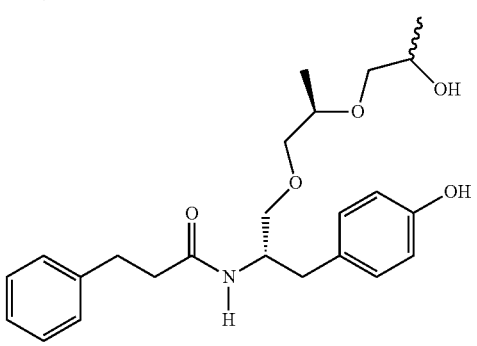
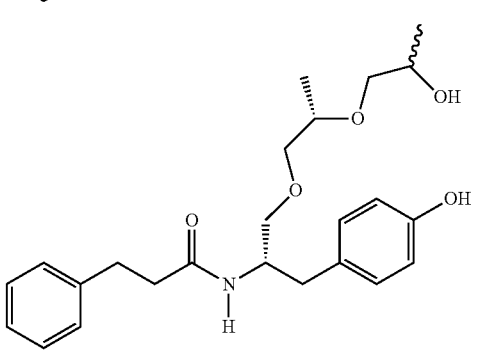

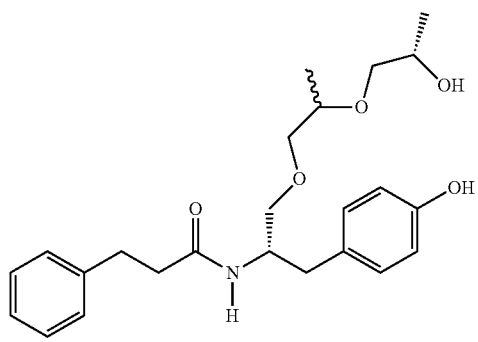
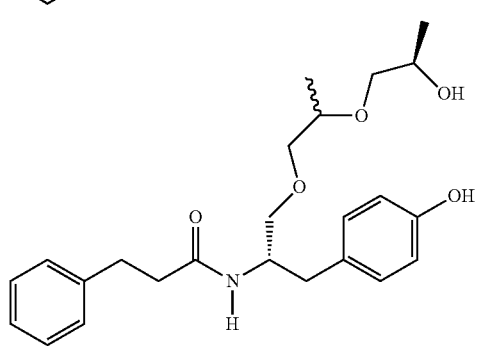
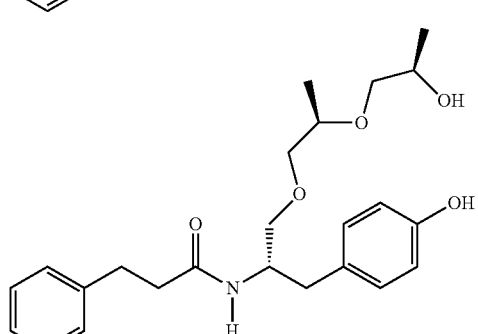
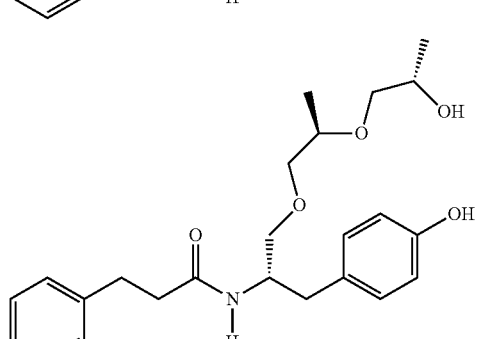
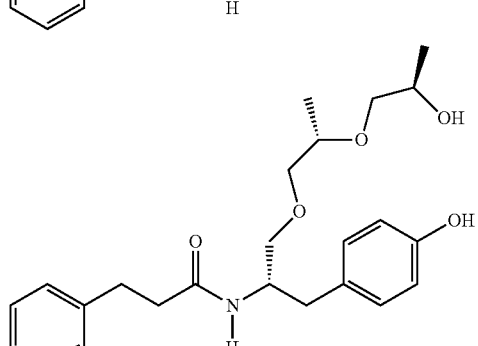
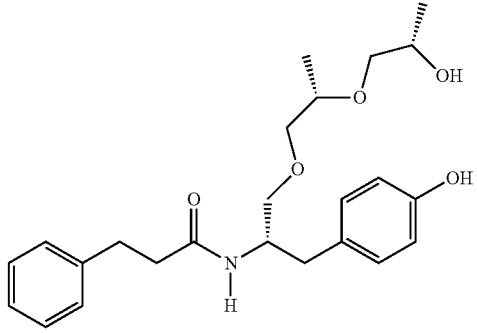
Isomeric forms of compound 1 also include geometric isomers as shown below, including all R and S permutations:
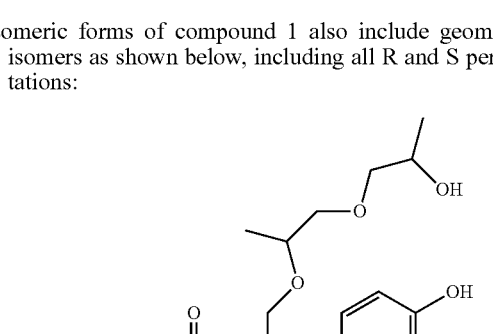
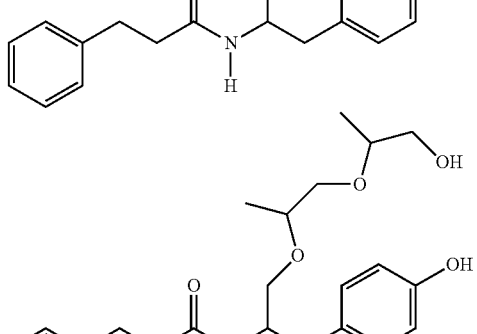
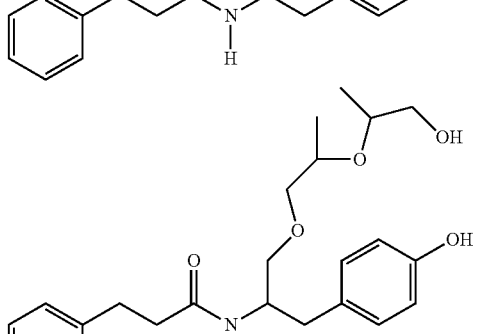
For example, some isomeric forms of compound 3 (NRD 175) are shown below:
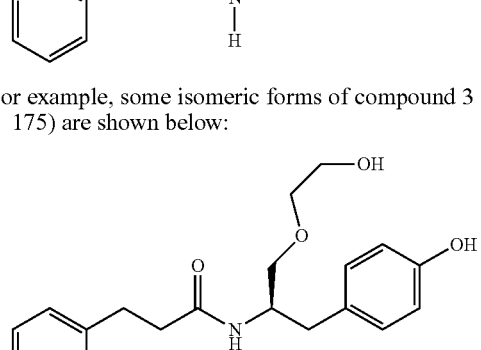

-continued

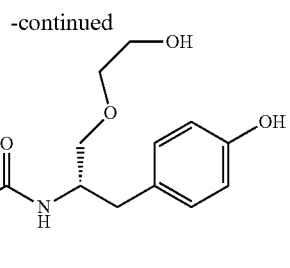

Suitable synthetic methods for obtaining and purifying the compounds of the present invention are disclosed in detail below. However, it should be apparent to a person skilled in the art that the compounds may be prepared using any other feasible synthetic methods.

The compounds of the invention may be synthesised as polyalkylene glycol (PAG) conjugates. Polymers that may be used for such conjugation include poly(ethylene glycol) (PEG), also known as or poly(ethylene oxide) (PEO) and polypropylene glycol (including poly isopropylene glycol).

A polyalkylene glycol (PAG), such as PEG, is a linear polymer terminated at each end with hydroxyl groups:

The above polymer, α,ω-dihydroxyl poly(ethylene glycol), can also be represented as HO-PEG-OH, where it is understood that the —PEG-symbol represents the following structural unit:

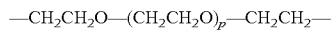

where p may range from 0 to about 48. PEG may be used as methoxy-PEG-OH, or mPEG, in which one terminus is the relatively inert methoxy group, while the other terminus is a hydroxyl group that is subject to ready chemical modification. Additionally, random or block copolymers of different alkylene oxides (e.g., ethylene oxide and propylene oxide) that are closely related to PEG in their chemistry may be substituted for PEG.

The PAG polymers may be linear or branched.

It is to be understood that compounds of the invention comprise a PAG moiety that may include a mixture of polymers which have a varying number of monomeric units. The synthesis of a PAG-conjugate compound may produce a population of molecules with a Poisson distribution of the number of monomeric units per polymer in the conjugate. Thus, a compound according to the invention that is described as having a polymer of n=2 monomeric units refers not only to the actual polymers in that population being described as having n=2 monomeric units, but also to a population of molecules with the peak of the distribution being 2 or close to 2. The distribution of monomeric units in a given population can be determined, e.g., by nuclear magnetic resonance (NMR) or by mass spectrometry (MS).

In yet another aspect of the present invention there is provided a pharmaceutical composition for use in the treatment or prophylaxis of pain, said composition comprising a pharmaceutically effective amount of one or more of the compounds of the invention. Said composition may further comprise one or more pharmaceutically acceptable excipients. In some embodiments, said composition may also comprise acetaminophen, one or more other NSAIDs, one or more weak or strong opioids, an antidepressant or an antiepileptic agent.

The pharmaceutical composition of the invention may comprise one or more of the compounds of the invention in a pure, substantially pure or partially pure form. In some embodiments, said substantially pure form may comprise at least 95% wt. of said one or more compounds, e.g., 96% wt., 97% wt., 98% wt. or more than 99% wt. of said compounds.

Said substantially or partially pure form of said compound(s) may further comprise a proportion of free polyalkylene glycol such, for example, as polyethylene glycol (PEG) or polypropylene glycol (PPG). Such polyalkylene glycol may itself be biologically active. The chain length of the free polyalkylene glycol may range from 1-50, preferably 1-25, more preferably 1-5 or 1 or 2. In some embodiments, said polyalkylene glycol may have a chain length of 1, 2, 3 4 or 5 monomeric units. Said free polyalkylene glycol may comprise a mixture of different chain lengths. Thus, for a substantially pure form of said one or more compounds, said form may comprise up to 5% wt. of free polyalkylene glycol, e.g., up to 4% wt., 3% wt., 2% wt. or less than 1% wt., with the total amount in said form of said one or more compounds and said free polyalkylene glycol being 100% wt.

Said partially pure form of said one or more compounds may comprise about 5-60% wt. of the one or more compounds according to the invention and about 95-40% wt. of free polyalkylene glycol, the total amount being 100% wt. Typically, said partially pure form may comprise about 45-55% wt. of said one or more compounds and about 55-45% wt. of said one or more polyalkylene glycols. Alternatively, said form may comprise about 80-95% wt. of said one or more compounds and about 20-5% wt. of said polyalkylene glycol(s).

Suitably, the composition of the invention may be formulated as a unit dosage form. Each unit dosage form may comprise all or a predetermined fraction of the daily dose amount of the one or more compounds of the invention, e.g., one half or one quarter of the daily dose amount.

Thus, the composition may be formulated as a tablet, a pill, a capsule, a powder, granules, a sterile parenteral solution or suspension, a metered aerosol or liquid spray, drops, an ampoule, an auto-injector device, a suppository, a cream or a gel. Said composition may be adapted for oral, enteral parenteral, intrathecal, intranasal, sublingual, rectal or topical administration, or for administration by inhalation or insufflation. Oral compositions such as tablets, pills, capsules or wafers are particularly preferred.

For preparing a solid dosage form such as a tablet, said one or more compounds may be mixed with one or more pharmaceutical excipients, e.g., conventional tabletting ingredients such as corn starch, lactose, sucrose, sorbitol, talc, stearic acid, magnesium stearate, dicalcium phosphate or gums, or other pharmaceutical diluents, e.g., water, to form a solid pre-formulation composition containing a substantially homogeneous mixture of said one or more compounds, such that said one or more compounds are dispersed evenly throughout the composition, so that the composition may be readily subdivided into equally effective unit dosage forms such as tablets, pills and capsules.

Said solid pre-formulation composition is then subdivided into unit dosage forms of the kind mentioned above which may each contain from 0.1 to about 500 mg of the one or more compounds. Favoured unit dosage forms contain from 1 to 500 mg, e.g., 1, 5, 10, 25, 50, 100, 300 or 500 mg, of the compound(s).

When formulated as a tablet or pill, said tablet or pill may be coated or otherwise compounded to provide a dosage form affording the advantage of prolonged action. For instance, said tablet or pill can comprise an inner dosage and an outer dosage component, the latter being in the form of an envelope over the former. These two components may be separated by an enteric layer that serves to resist disintegration in the stomach and permits the inner component to pass intact into the duodenum or to be delayed in release. A variety of materials are known in the use in such enteric layers or coatings, such materials including a number of polymeric acids and mixtures of polymeric acids with such materials as shellac, cetyl alcohol and cellulose acetate.

Alternatively, the pharmaceutical composition of the present invention may be formulated as a liquid dosage form for administration orally or by injection; for example an aqueous solution, a suitably flavoured syrup, an aqueous or oil suspension or a flavoured emulsion with edible oils such, for example, as cottonseed oil, sesame oil, coconut oil or peanut oil, as well as an elixir or a similar pharmaceutical vehicle. Suitable dispersing or suspending agents for an aqueous suspension include synthetic and natural gums, e.g., tragacanth, acacia, alginate, dextran, sodium carboxymethylcellulose, methylcellulose, polyvinyl-pyrrolidone or gelatin.

The following is a description by way of example only with reference to the accompanying drawings of embodiments of the present invention.

DETAILED DESCRIPTION

Figure 1A:
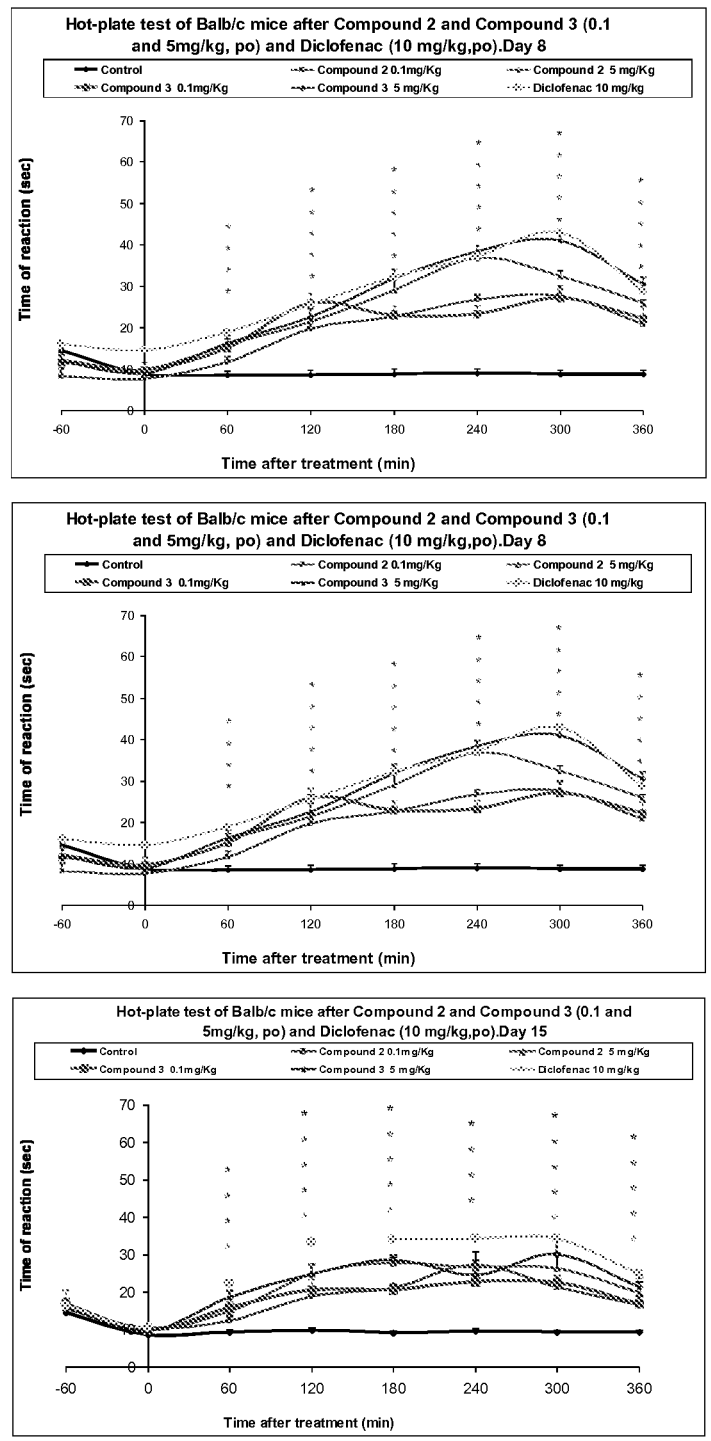
FIG. 1a provides graphs showing the results (time of reaction vs. time after treatment) of a Hot-Plate Test using Balb/c mice following administration of Compound 2 or 3 of the invention.

The present invention relates to methods for treating or preventing pain in a human or non-human animal patient in need thereof, which the method comprises administering to said patient a therapeutically effective amount of at least one compound represented by formula I:

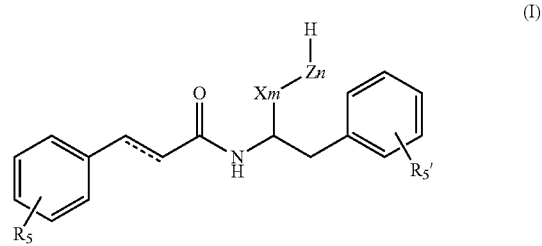

(I)

wherein:
⁓ represents a single or a double bond;
$R_5$ and $R_5'$ are independently —H, —OH or —$OR_6$, wherein $R_6$ is a linear or branched $C_1$-$C_4$ alkyl;

X is —CH$_2$O—;
Z is —CH$_2$CH$_2$O—, —CH(CH$_3$)CH$_2$O— or —CH$_2$CH(CH$_3$)O—;
m is 1; and
n is an integer of 1, 2, 3, 4, or 5;
or a pharmaceutically acceptable salt, prodrug, metabolite, or hydrate thereof.

The present invention relates to a method for the treatment of acute or chronic pain. The present invention relates to a method for the treatment of nociceptive pain or neuropathic pain.

The present invention relates to a method for the treatment or prevention of pain, wherein the compound administered is represented by formula II:

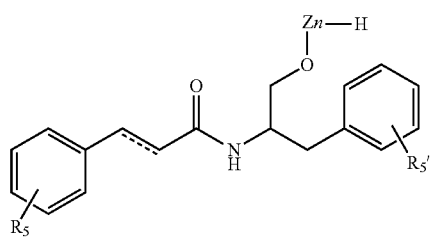

(II)

or a pharmaceutically acceptable salt prodrug, metabolite, or hydrate thereof. The present invention relates to a method, wherein Z is —CH$_2$CH(CH$_3$)O—.

The present invention relates to a method, wherein the compound administered is represented by formula III:

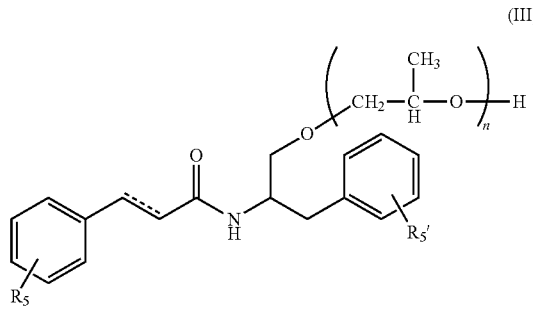

(III)

or a pharmaceutically acceptable salt, prodrug, metabolite, or hydrate thereof.

The present invention relates to a method, wherein R$_5$ is H or OH. The present invention relates to a method, wherein R$_5$' is H or OH. The present invention relates to a method, wherein n is 1 or 2.

The present invention relates to a method, wherein the compound is represented by formula IV, V, VI or VII:

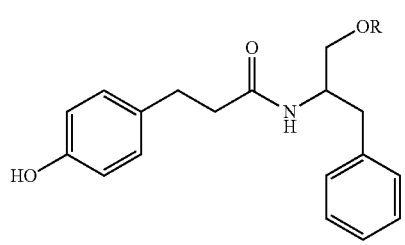

(IV)

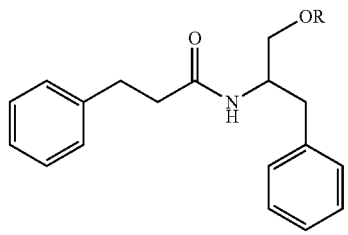

(V)

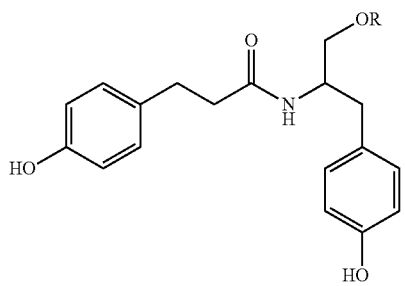

(VI)

or

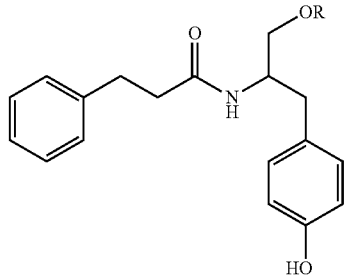

(VII)

or a pharmaceutically acceptable salt, prodrug, metabolite, or hydrate thereof,
wherein R is a polyalkylene glycol polymer having n units, wherein n is an integer of 1, 2, 3, 4, or 5.

The present invention relates to a method, wherein the compound is administered as a pharmaceutical composition comprising a therapeutically effective amount of one or more of the compounds represented by formulae I, II, III, IV, V, VI, or VII together with one or more pharmaceutically acceptable excipients.

The present invention relates to a method, wherein the composition administered comprises said one or more compounds in substantially pure form, said substantially pure form consisting of at least 95% wt. of said one or more compounds and up to 5% wt. of free polyalkylene glycol, with the total amount in said form of said one or more compounds and said free polyalkylene glycol being 100% wt.

The present invention relates to a method, wherein the composition administered comprises said one or more compounds in partially pure form, said partially pure form consisting of about 5-60% wt. of the one or more compounds and about 95-40% wt. of free polyalkylene glycol, the total amount being 100% wt.

The present invention relates to a method, wherein the composition is formulated as a unit dosage form. The present invention relates to a method, wherein the composition is formulated for oral administration. The present invention relates to a method, wherein the composition is formulated as a unit dosage form comprising from 0.1 to about 500 mg of the one or more compounds. The present invention relates to a method, wherein a daily dose of 1.0 mg to 15 g of said one or more compounds is administered. The present invention relates to a method, wherein the one or more compounds are administered orally.

Synthesis of Polyalkylene Glycol Compounds

Polyalkylene glycol compounds were generally synthesised by preparation of the appropriate alcohol compound followed by conjugation of the alcohol with a polyalkylene glycol (PAG) polymer (e.g., polyethylene glycol (PEG) or polypropylene glycol (PPG)) of the desired length.

Synthesis a: Compound a (phenyl alaminol)

1.2 g, 32 mM, of LiAlH$_4$ were added to 2.3 g, 10 mM, phenyl alanine ethyl ester HCl in 50 ml dry ether. After stirring for 2 hours at room temperature, water and KOH were added and the reaction product was extracted with ethyl acetate. After evaporation, 0.8 g of Compound a, a light yellow oil, was obtained.

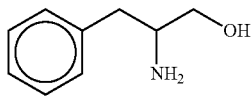

a $C_9H_{13}NO$
Mol. Wt.: 151.21

Compound a crystallised on standing. Mp-70.

NMR CDCl$_3$ 7.30 (5H, m), 3.64 (1H, dd, J=10.5, 3.8 Hz) 3.40 (1H, dd, J=10.5, 7.2 Hz) 3.12 (1H, m), 2.81 (1H, dd, J=13.2, 5.2 Hz), 2.52 (1H, dd, J=13.2, 8.6 Hz)

NMR acetone d$_6$ 7.30 (5H, m), 3.76 (1H, dt) 3.60 (1H, m) 3.30 (1H, t), 2.85 (2H, m). *Helv. Chim. Acta,* 31, 1617 (1948). Biels.-E3, Vol. 13, p 1757.

Synthesis b: Compound b (tyrosinol)

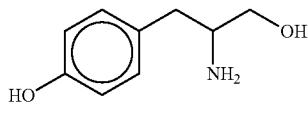

$C_9H_{13}NO_2$
Mol. Wt.: 167.21

To 3 g, 12 mM, L-tyrosine ethyl ester HCl in 50 ml dry ether was added 1.2 g 32 mM LiAlH$_4$. After stirring 3 hours at room temperature, water and KOH were added and the reaction was extracted with ethyl acetate. Evaporation gave 1.1 g of a light yellow oil, 54% yield, which on standing crystallized. mp-85.

NMR CDCl$_3$ 7.20 (4H, AB q, J=8.6 Hz), 3.50 (2H, m) 3.20 (1H, m), 2.81 (2H, m).

NMR tyrosine ethyl ester free base CDCl$_3$ 7.0, 6.56 (4H, AB q, J=8.8 Hz), 4.20 (2H, q, J=7.0 Hz), 3.70, 3.0, 2.80 (3H, 12 line ABXm), 1.28 (3H, t, J=7.0 Hz). *JACS* 71, 305 (1949). Biels.-E3, Vol. 13, p 2263.

Synthesis 1: Compound 2

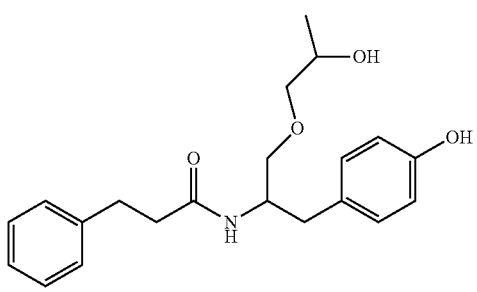

Compound 2 (NRD135) has the structure of general formula IV, with R=PPG and n=1. MW=354

Compound 2 was synthesised as follows.

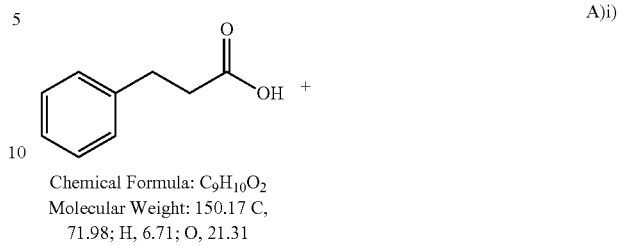

A)i)

Chemical Formula: $C_9H_{10}O_2$
Molecular Weight: 150.17 C, 71.98; H, 6.71; O, 21.31

Hydrocinnamic Acid

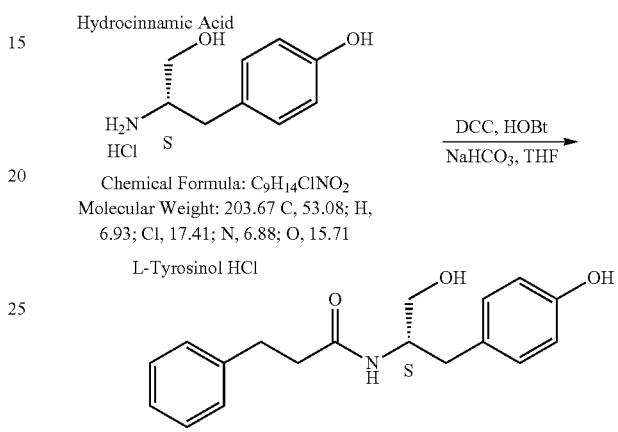

Chemical Formula: $C_9H_{14}ClNO_2$
Molecular Weight: 203.67 C, 53.08; H, 6.93; Cl, 17.41; N, 6.88; O, 15.71

L-Tyrosinol HCl

Chemical Formula: $C_{18}H_{21}NO_3$
Molecular Weight: 299.36 C, 72.22; H, 7.07; N, 4.68; O, 16.03

AV74S 4037-6

L-tyrosinol (24.4 g) was reacted with hydrocinnamic acid (HCA, 1.02 eq), DCC (1.1 eq), HOBT (1.1 eq) and NaHCO$_3$ (4.0 eq) at room temperature overnight. Reaction was completed overnight at RT. The reaction was filtered and a solvent swap from THF to EA was performed. The EA layer was washed with 1N HCl, sat NaHCO$_3$, Brine, and organic layer dried over Na$_2$SO$_4$. Removal of a portion of EA was conducted via distillation, then slow addition of heptane afforded 33.82 g (94.1% yield) of desired product. HPLC: Purity=≥92%.

ii)

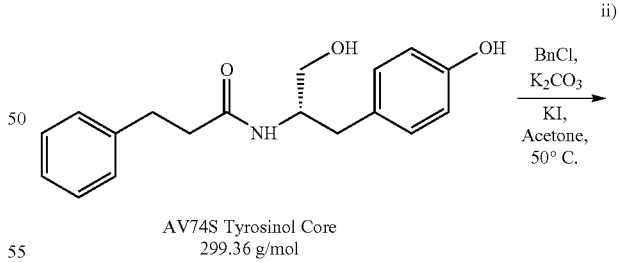

AV74S Tyrosinol Core
299.36 g/mol

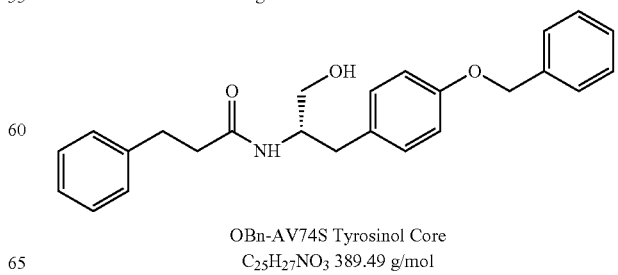

OBn-AV74S Tyrosinol Core
$C_{25}H_{27}NO_3$ 389.49 g/mol

The benzyl ether of AV74S was prepared. 1.33 eq benzyl chloride was charged to AV74S (50.90 g), 1.33 eq potassium carbonate, 0.1 eq potassium iodide in acetone at 50° C. After 20 hours at 50° C., the reaction was heated to reflux for an additional 7 hours to consume all the starting material. The reaction was cooled to room temperature and quenched with water. The slurry was cooled to <5° C. and stirred for 1.5 hours, then filtered. The solids were dried in vacuo (70° C.) over the weekend to afford 62.98 g of crude solids. The AUC purity was 94.4%. $^1$H NMR analysis supports the assigned structure.

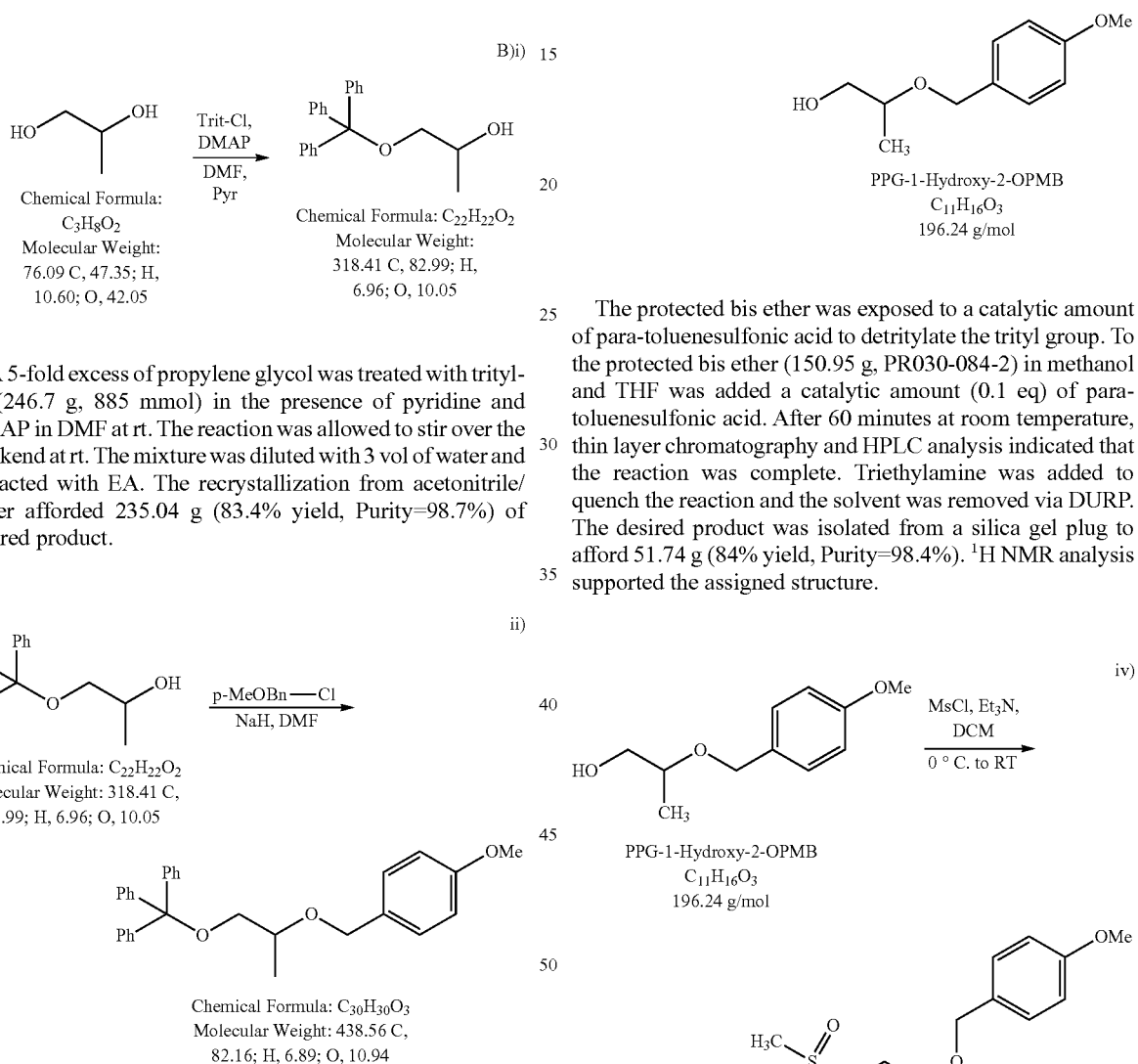

A 5-fold excess of propylene glycol was treated with trityl-Cl (246.7 g, 885 mmol) in the presence of pyridine and DMAP in DMF at rt. The reaction was allowed to stir over the weekend at rt. The mixture was diluted with 3 vol of water and extracted with EA. The recrystallization from acetonitrile/water afforded 235.04 g (83.4% yield, Purity=98.7%) of desired product.

The trityl ether (99.82 g, 313.5 mmol) was converted into the orthogonally protected bis ether. To a <10° C. slurry of 2 equiv of NaH in DMF was added dropwise trityl ether at a rate to control gas evolution. After stirring for 15 minutes at <10° C., p-methoxybenzyl chloride was added via syringe. The mixture was warmed to rt (mildly exothermic) and allowed to stir at rt for 1.5 hours. HPLC analysis indicated complete consumption of starting material. Workup consisted of careful quenching of the mixture with 3 volumes of water and EA extraction. The EA layers were washed with water to remove DMF and dried over $Na_2SO_4$ to give a hazy oil (150.95 g,).

The protected bis ether was exposed to a catalytic amount of para-toluenesulfonic acid to detritylate the trityl group. To the protected bis ether (150.95 g, PR030-084-2) in methanol and THF was added a catalytic amount (0.1 eq) of para-toluenesulfonic acid. After 60 minutes at room temperature, thin layer chromatography and HPLC analysis indicated that the reaction was complete. Triethylamine was added to quench the reaction and the solvent was removed via DURP. The desired product was isolated from a silica gel plug to afford 51.74 g (84% yield, Purity=98.4%). $^1$H NMR analysis supported the assigned structure.

The mesylation of PPG-1-Hydroxy-2-OPMB (20.1 g) was conducted using 2.0 eq of methanesulfonyl chloride and 2.25 eq of triethylamine at <5° C. to give a clean conversion to desired product in 108% crude yield as an oil. This material was sufficiently pure to use for next steps.

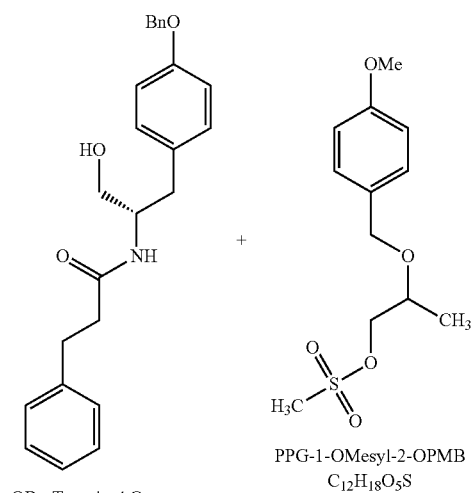
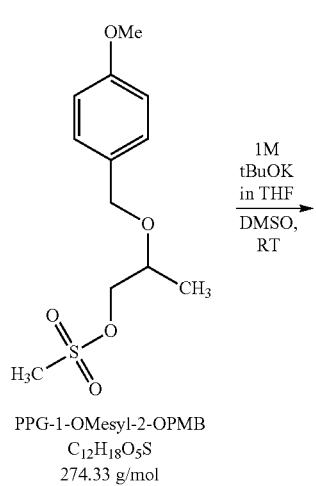
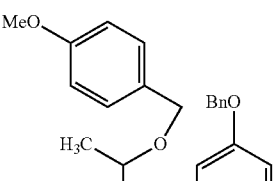
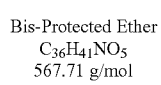
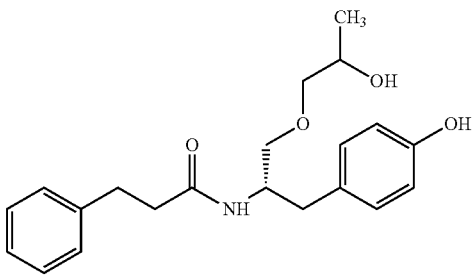

20.13 g OBn-Tyrosinol core (from step A) and 2.25 eq PPG-1-OMesyl-2-OPMB (from step B) in DMSO was added 2.0 eq of 1M potassium tert-butoxide (in THF) over 1.6 hours at room temperature. After 15.5 hours at room temperature, 91.9% of desired product had formed and 8.1% of OBn-Tyrosinol core was not fully consumed. An additional 0.3 eq of 1M potassium tert-butoxide was added and the reaction was allowed to stir at 45° C. After an additional 18 hours at 45° C., 98.3% of desired product had formed and 1.7% of OBn-Tyrosinol core was not fully consumed. The reaction mixture was quenched with USP water at room temperature and extracted with ethyl acetate. The combined organic layers were successively washed with USP water, saturated aqueous NaHCO3 solution, brine, and dried over sodium sulfate to afford 39.00 g of an oil. An attempt to recrystallize from toluene/heptane proved to be unsuccessful and provided 25.8 g of solids that were 77.4% pure of desired product.

Celite was added to 25.3 grams of PR030-114-12 dissolved in hot MTBE/Heptane (1:1). This mixture was filtered hot over a bed of Celite. The filtrate was cooled to room temperature and the solids were collected via vacuum filtration to provide 13.1 g of white solids (52.4% yield). A second crop was obtained giving an additional 2.75 g of white solids (an additional 11% yield). The purity of these two crops was 98.8% and 98.1%, respectively. 1H NMR and Mass spec analysis supported the assigned structure for desired product. The combined yield was 63.5%.

The bis-protected ether (15.7 g) was exposed to one-pot hydrogenation-debenzylation conditions (10% loading of 10% Pd/C and 0.25 eq of p-toluenesulfonic acid) in methanol. After 2 hours at 60° C. under a hydrogen atmosphere, HPLC analysis indicated that the hydrogenation of the benzyl and the debenzylation of PMB ring was complete. The reaction mixture was filtered over Celite and concentrated under reduced pressure. The residue was dissolve in ethyl acetate and a saturated aqueous sodium bicarbonate treatment was conducted to effectively remove p-toluenesulfonic acid, then DURP to provide 12.13 g of an oil (PR030-120-4). Desired product was isolated from an EA/Heptane recrystallization to provide 8.83 g of a white solid (PR030-120-6, 89.4% yield). The purity of PR030-120-6 was 99.3% via HPLC analysis. 1H NMR and Mass spec analysis supported the assigned structure for desired product.

Synthesis 2: Compound 1

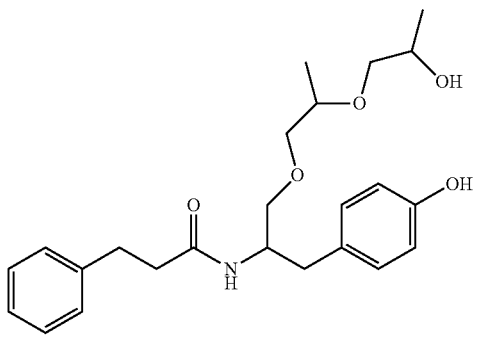 [SMILES: CC(O)COC(C)COCC(Cc1ccc(O)cc1)NC(=O)CCc1ccccc1]

Compound 1 has the structure of general formula IV, with R=PPG and n=2. MW=413 Compound 1 was prepared using the same procedure as described above in Synthesis 1, with the substitution of the PPG, n=1 for PPG, n=2.

It will be understood that the procedures of Synthesis 1 can therefore be applied to produce compounds of formula VII in which Z is PPG. Alternative compounds falling within formula I can be produced by substitution of L-tyrosinol in step (A) with the appropriate amino alcohol (e.g. phenyl alaminol as produced in synthesis a)).

The procedures of Synthesis 1 can also be adapted as described below in Synthesis 3 so that they result in the production of a compound of formula 1 in which Z is PEG.

Synthesis 3: Compound 3

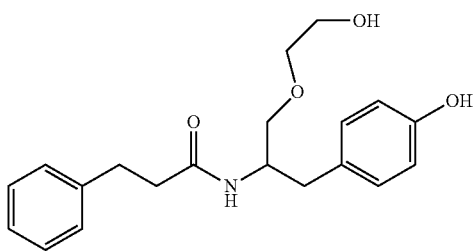 [SMILES: O=C(CCc1ccccc1)NC(COCCO)Cc1ccc(O)cc1]

Compound 3 has the structure of general formula IV, with R=PEG and n=1. MW=413 Compound 3 was prepared using the following procedure.
A) Step A was performed as for compound 2.

A 5-fold excess of ethylene glycol was treated with trityl-Cl (22.9 g, 82.13 mmol) in the presence of pyridine and DMAP in DMF at rt. The reaction was allowed to stir overnight at room temperature. The mixture was diluted with 3 vol of water and extracted with EA. Isolation of desired product via recrystallization from acetonitrile/water gave 22.87 g of solids (91.5% yield). The purity determined by HPLC was 97.8%. 1H NMR and Mass Spec analysis supported the assigned structure for desired product.

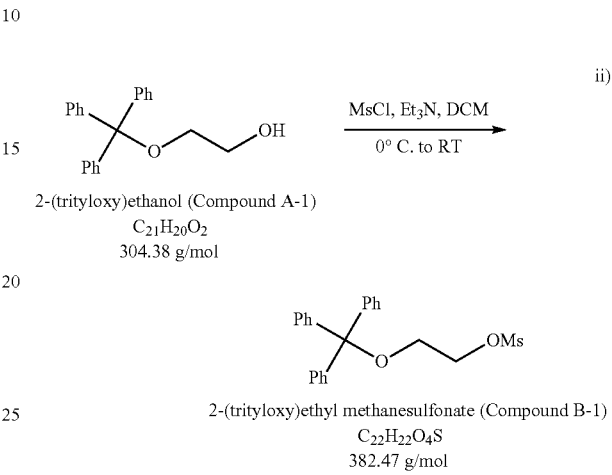

The mesylation of compound A-1 (11.00 g) was conducted using 2.0 eq of methanesulfonyl chloride and 2.25 eq of triethylamine at <5° C. to give a clean conversion to desired product in quantitative yield as a solid (13.85 g). AUC purity=97.5%. Mass spec and $^1$H NMR analysis supported the assigned structure.

C)i) 2.29 g of OBn-Tyrosinol core (from step A) and 2.25 eq of Compound B-1 (from Step B) in DMSO was added 2.0 eq of 1M potassium tert-butoxide (in THF) over 45 mins at room temperature. After 12.25 hours at 35° C., the reaction mixture was quenched with USP water at room temperature and extracted with ethyl acetate. The combined organic layers were successively washed with USP water, saturated aqueous NaHCO$_3$ solution, brine, and dried over sodium sulfate to afford 5.05 g as an oil. This product was purified via column chromatography to isolate the desired product as a solid (2.07 g). AUC purity=97.5%. $^1$H NMR analysis supported the assigned structure for desired product.

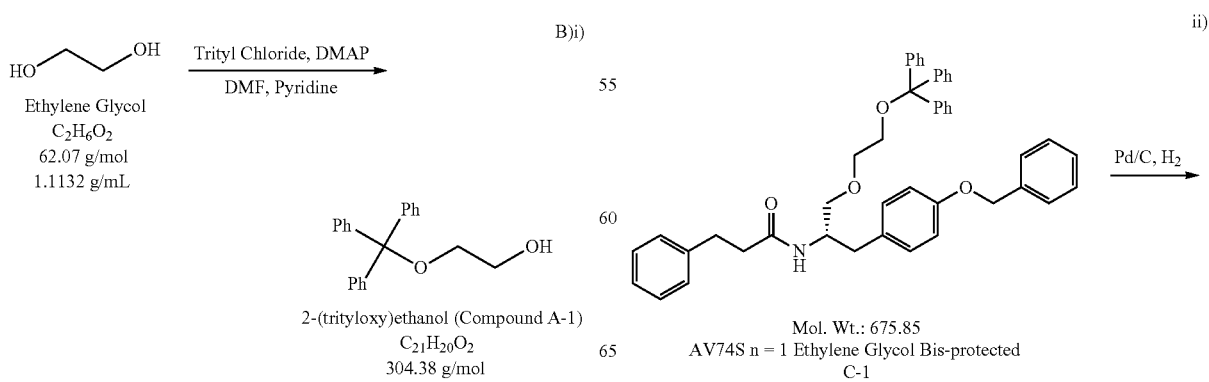

-continued

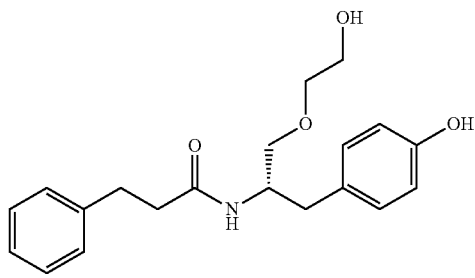

Mol. Wt.: 343.42
AV74S n = 1 Ethylene Glycol
D-1

2.07 g C-1. C-1 was dissolved in 30 vol methanol at 60 C. 10 wt % Pd/C then 0.25 eq pTSA was added while at 60 C. Hydrogen atmosphere was maintained for 3 hours. The catalyst was removed by hot filtration. The filtrate was DURP to obtain a solid. The solids were dissolved in ethyl acetate and washed with sodium bicarbonate. The organic was dried over sodium sulfate and DURP to give gooey solids.

EXAMPLES

The experiments described below were conducted to demonstrate the utility of compounds of the invention in the treatment of pain.

Example 1

Antinociceptive Effect of Compound 2 and Compound 3

The objective of the study was to assess antinociceptive activity of tested items in the hot plate tests in mice, when administered sub-chronically. Measuring paw licking or jumping response time elapses following placement on heated surface (hot plate) was used to determine potential antinociceptive effect in mice.

A total of 42 Balb/c mice (12 weeks old) were utilized. The mice were approximately 25 g males at study initiation. The minimum and maximum weights of the group were within a range of ±10% of group mean weight.

Compounds 2 and 3 were tested and compared with Diclofenac® (Perigo). DMSO solutions were used. Six groups of mice (each having n=7 or n=8 mice) were tested, the last group receiving Diclofenac®.

| Animal group | Dose volume | Testing at: Time/min | Dose mg/kg/day |
|---|---|---|---|
| 1M (sham) (7) DMSO | 10 ml/kg | −60, 0, 60, 120, 180, 240, 300, 360 | None |
| 2M + 3M (7 + 7) compound 2 [1unit] | | | 0.1; 5 |
| 4M + 5M (7 + 7) Compound 3 [1unit] | | | 0.1; 5 |
| 6M (8) Diclofenac ® | | | 10 |

Formulations according to the following table were prepared for administration to the groups of mice.

| Formulation | Composition |
|---|---|
| 1 | Control - 0.02% DMSO 0.3 ml/mouse, po (3 ml/10 mice) (0.6 μl DMSO + 2999.4 μl DDW), n = 8. |
| 2 | Compound 2, 0.1 mg/Kg = 0.003 mg/0.3 ml/mouse, po (3 ml/10 mice) (compound 2, 0.03 mg (Stock 50 mg/1 ml DMSO) 0.6 μl + 2999.4 μl DDW), n = 8 |
| 3 | Compound 2, 5 mg/Kg = 0.15 mg/0.3 ml/mouse, po (3 ml/10 mice) (compound 2 1.5 mg (Stock 50 mg/1 ml DMSO) 30 μl + 2970 μl DDW), n = 8 |
| 4 | Compound 3, 0.1 mg/kg = 0.003 mg/0.3 ml/mouse, po (3 ml/10 mice) (compound 3, 0.03 mg (Stock 50 mg/1 ml DMSO) 0.6 μl + 2999.4 μl DDW), n = 8 |
| 5 | Compound 3, 5 mg/Kg = 0.15 mg/0.3 ml/mouse, po (3 ml/10 mice) (compound 3 1.5 mg (Stock 50 mg/1 ml DMSO) 30 μl + 2970 μl DDW), n = 8 |
| 6 | Diclofenac ® 10 mg/kg = 0.3 mg/0.3 ml/mouse, po (3 ml/10 mice) from stock (Diclofenac ® 51 mg + 51000 μl DDW), n = 8 |

All groups received the drugs daily po for 16 days. Hot plate experiments were performed on days; 1, 8 and 15.

The following parameters were examined: body weight (days 1, 8 15); open field on day 16 including distance moved, velocity, immobility, rearings, time in center and other parameters. After the last experiment (i.e., open field day 16), animals were sacrificed by decapitation and blood was collected 24 hr after last drug administration. The following organs were dissected: liver (gall bladder), spleen, lungs, brain, heart and kidney for toxicity examination (formaldehyde 4%).

The hot plate is maintained thermostatically at a temperature of 52° C. One hour before the administration of the drugs, mice are tested in the hot plate. At time 0 the mice are administered with the test compound and the response to the hot plate is measured again at different times: 60, 120, 180, 240, 300 and 360 min.

Results are expressed as: Delta from maximum response [baseline vs. maximum response]; Absolute measures over time; and Accumulated time.

Figure 1B:
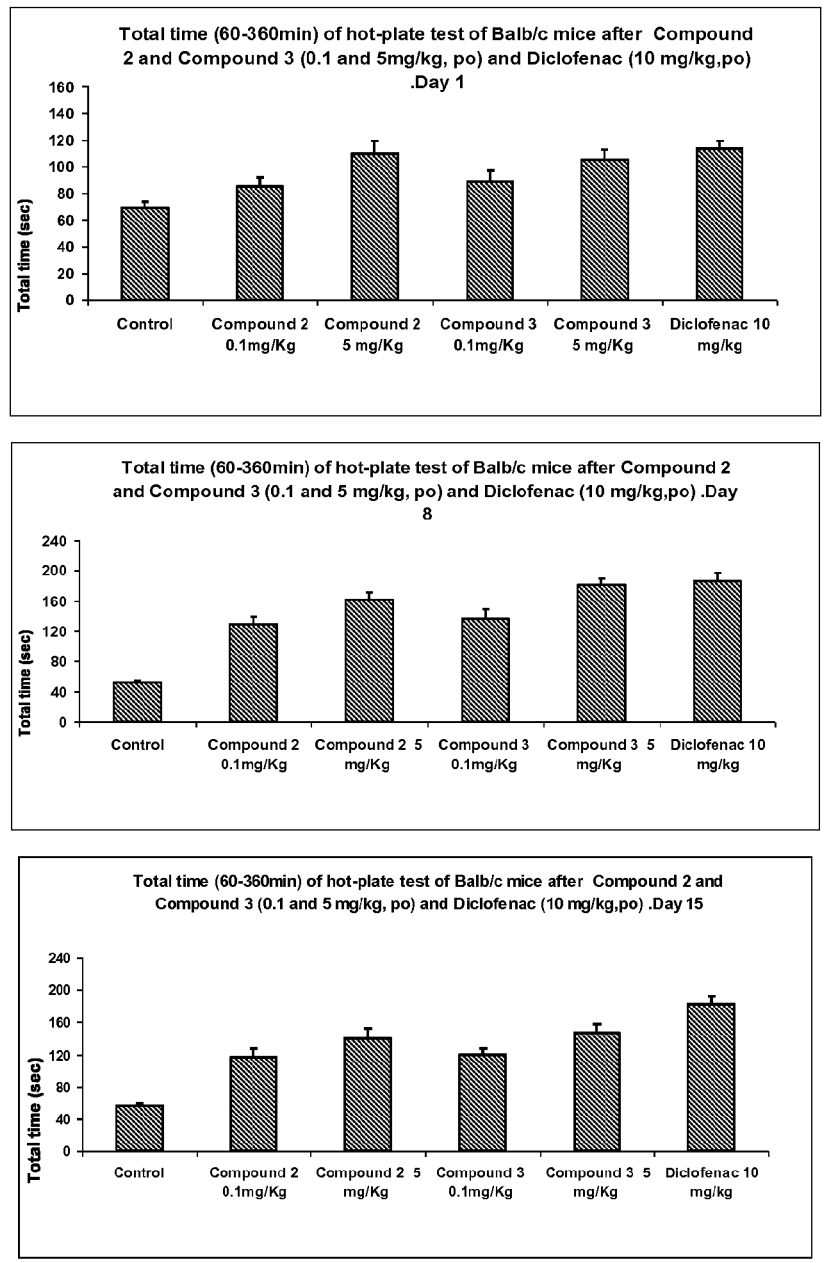
FIG. 1b provides graphs showing the results (total time vs. formulation) of a Hot-Plate Test using Balb/c mice following administration of Compound 2 or 3 of the invention.

FIGS. 1a and 1b provide graphical results showing a comparison of compounds 2 and 3 with Diclofenac® at days 1, 8, and 15.

Figure 1C:
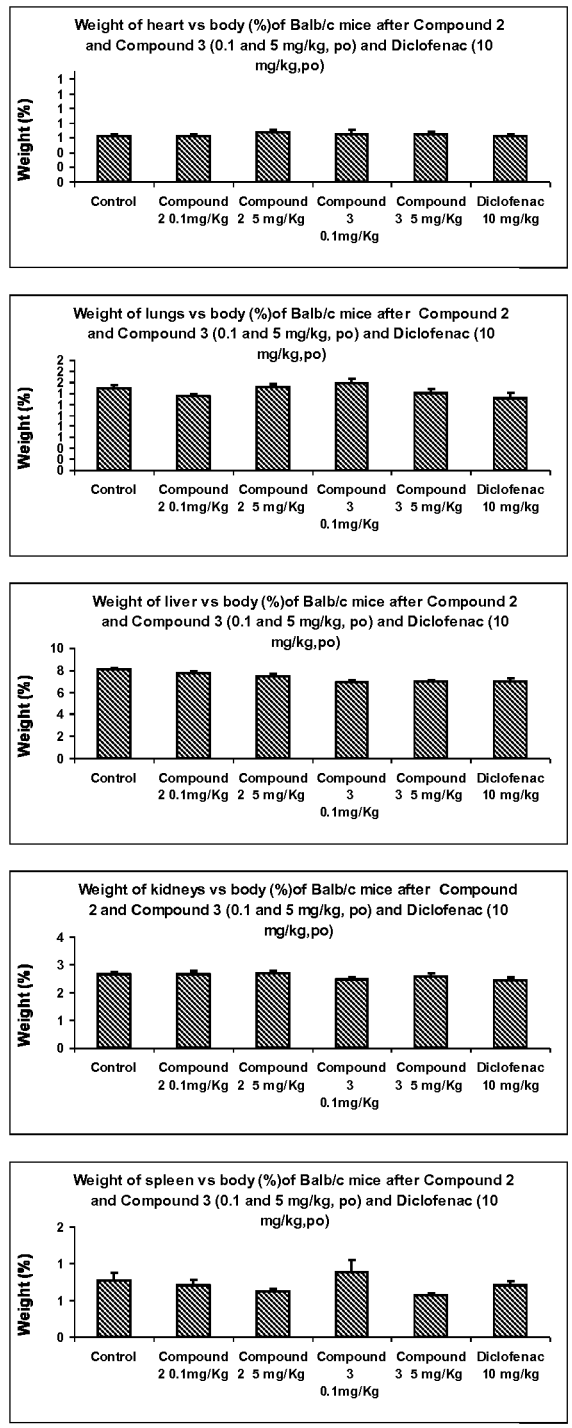
FIG. 1c provides graphs showing the results (weight of organs vs. formulation) of a Hot-Plate Test using Balb/c mice following administration of Compound 2 or 3 of the invention.

FIG. 1c shows internal organ weight data after administration of the tests.

Figure 1D:
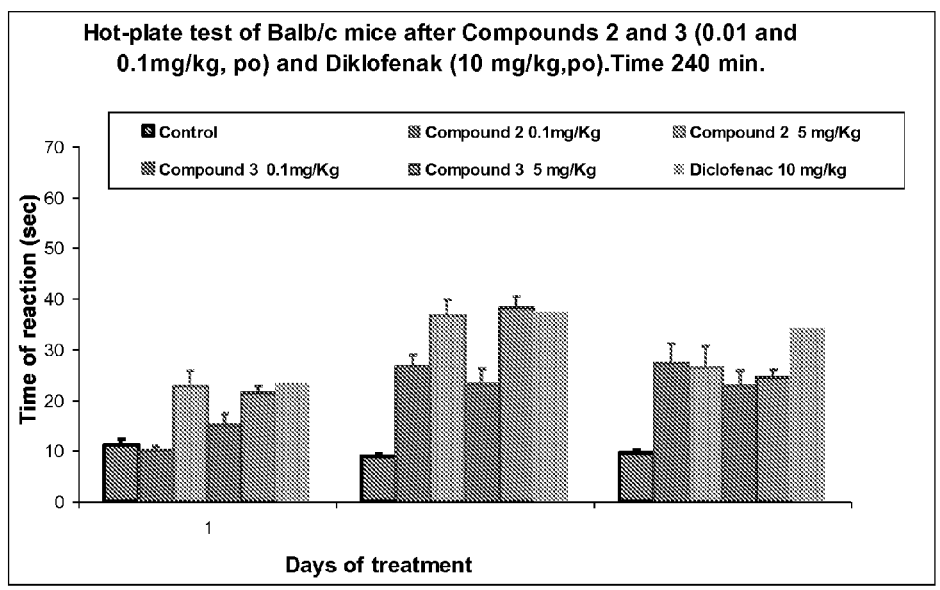
FIG. 1d provides a graph showing the results (time of reaction vs. formulation) of a Hot-Plate Test using Balb/c mice following administration of Compound 2 or 3 of the invention.

Additional data showed that compositions 2-5 significantly increased the time to reaction as compared with the control. A sample of such data is provided in FIG. 1d.

These data show that compounds 2 and 3 are effective as pain relievers.

Example 2

Nociceptin Activity Using Compound 2

Using the procedure outlined in Example 1, 40 male mice (Balb/c, 9 weeks old, naïve), were divided in 5 groups (8 mice per group) and treated daily (0 min, p.o.) with the formulations shown in the following table.

| Formulation | Composition |
|---|---|
| 1 | Control - 0.2% DMSO 0.3 ml/mouse, po (3 ml/10 mice) (6 µl DMSO + 2994 µl DDW), n = 8. |
| 2 | Compound 2, 0.01 mg/Kg = 0.0003 mg/0.3 ml/mouse, po (3 ml/10 mice) (Compound 2, 0.003 mg (Stock 50 mg/1 ml DMSO) 0.06 µl + 2999.94 µl DDW), n = 8 |
| 3 | Compound 2, 0.1 mg/Kg = 0.003 mg/0.3 ml/mouse, po (3 ml/10 mice) (Compound 2, 0.03 mg (Stock 50 mg/1 ml DMSO) 0.6 µl + 2999.4 µl DDW), n = 8 |
| 4 | Compound 2, 1 mg/kg = 0.03 mg/0.3 ml/mouse, po (3 ml/10 mice) (Compound 2, 0.3 mg (Stock 50 mg/1 ml DMSO) 6 µl + 2994 µl DDW), n = 8 |
| 5 | Compound 2, 0.1 mg/Kg = 0.003 mg/0.3 ml/mouse, i.p. (3 ml/10 mice) (Compound 2, 0.03 mg (Stock 50 mg/1 ml DMSO) 0.6 µl + 2999.4 µl DDW), n = 8 |

The animals were determined on the hotplate at: −60, 0, 120, 240, 360, 420 and 480 min. The hotplate mean temperature was 52 degrees±1.

Figure 2A:
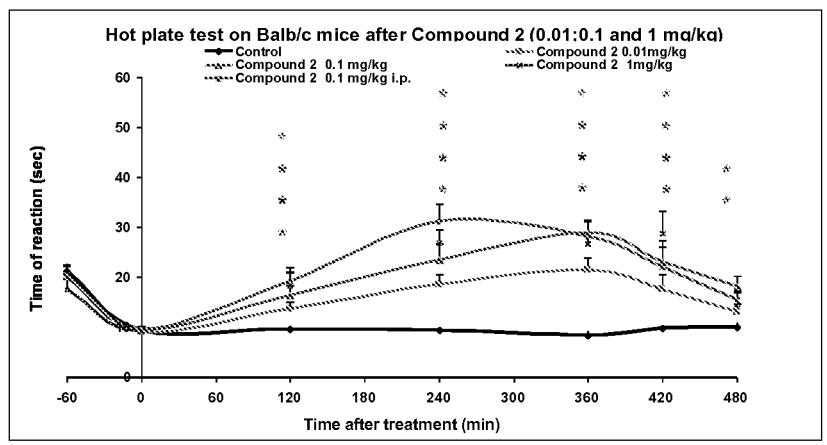
FIG. 2a provides graphs showing the results (time of reaction vs. time after treatment) of a Hot-Plate Test using Balb/c mice following administration of Compound 2 of the invention.
Figure 2B:
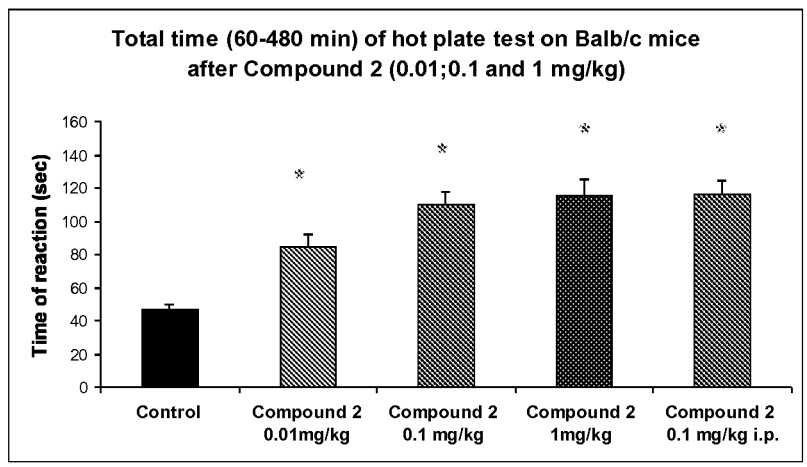
FIG. 2b provides graphs showing the results (total time vs. formulation) of a Hot-Plate Test using Balb/c mice following administration of Compound 2 of the invention.

FIGS. 2a and 2b provide data for these tests.

Example 3

Nociceptin Activity Using Compound 2

Using the procedure outlined in Example 1, 40 male mice (Balb/c, 9 weeks old, naïve), were divided in 5 groups (8 mice per group) and treated daily (0 min, p.o.) with the formulations shown in the following table.

| Formulation | Composition |
|---|---|
| 1 | Control - DDW + 2.5% DMSO 0.25 ml/mouse, po (2.5 ml/10 mice) (63 µl DMSO + 2437 µl DDW), n = 8. |
| 2 | Compound 2, eqM 25 (12.5) mg/Kg = 0.3125 mg/0.25 ml/mouse, po (2.5 ml/10 mice) ((Compound 2 3.125 mg (Stock 50 mg/1 ml DMSO) 63 µl + 2437 µl DDW) |
| 3 | Compound 2 eqM 12.5 (6.25) mg/Kg = 0.15625 mg/0.25 ml/mouse, po (2.5 ml/10 mice) ((Compound 2 1.5625 mg (Stock 50 mg/1 ml DMSO) 32 µl + 2468 µl DDW) |
| 4 | Compound 2 eqM 6.25 (3.125) mg/Kg = 0.078 mg/0.25 ml/mouse, po (2.5 ml/10 mice) ((Compound 2 0.78 mg (Stock 50 mg/1 ml DMSO) 16 µl + 2484 µl DDW) |

The animals were determined on HP at: −60, 0, 60, 120, 180, 240, 300 and 360 min. The hot-plate means the temperature of 52 degrees±1.

Figure 3A:
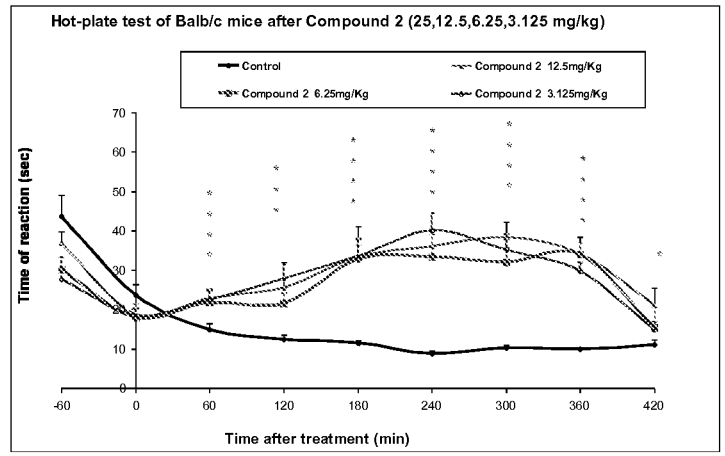
FIGS. 3a and 3b provide graphs showing the results (time of reaction vs. time after treatment) of a Hot-Plate Test using Balb/c mice following administration of Compound 2 of the invention.
Figure 3B:
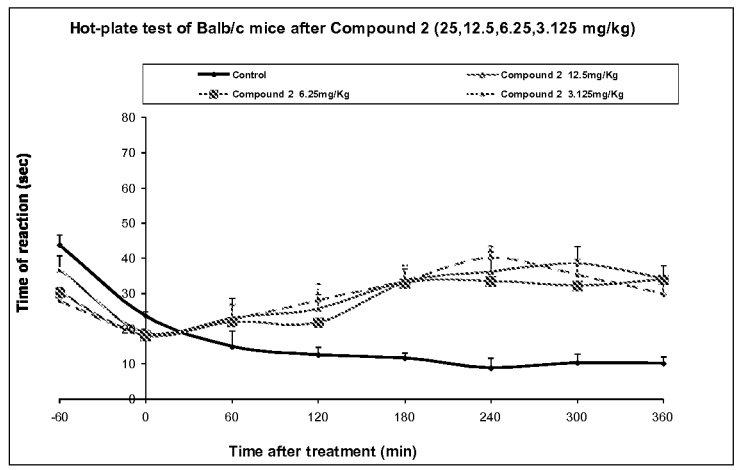
Figure 3C:
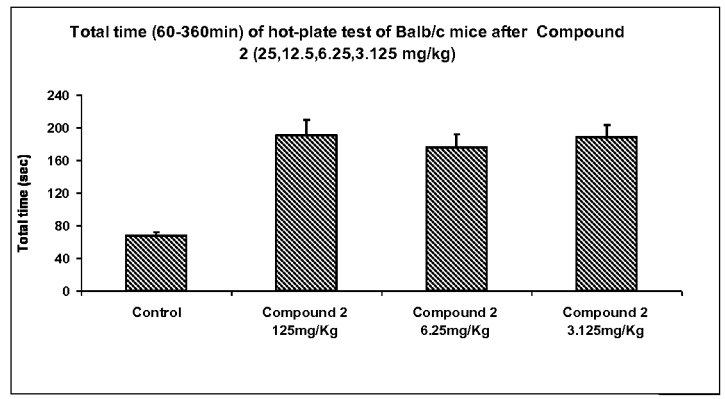
FIG. 3c provides a graph showing the results (total time vs. formulation) of a Hot-Plate Test using Balb/c mice following administration of Compound 2 of the invention.

FIGS. 3a, 3b, and 3c provide data for this test.

Example 4

Nociceptin Activity Using Compound 2

Using the procedure outlined in Example 1, 40 male mice (Balb/c, 13 weeks old, not naïve), were divided in 5 groups (8 mice per group) and treated daily (0 min, p.o.) with the formulations shown in the following table.

| Formulation | Composition |
|---|---|
| 1 | Control - DDW + 0.2% DMSO 0.3 ml/mouse, po (3 ml/10 mice) (6 μl DMSO + 2994 μl DDW), n = 8. |
| 2 | Compound 2 (Mw 357) 1 mg/Kg = 0.03 mg/0.3 ml/mouse, po (3 ml/10 mice) ((Compound 2 0.3 mg (Stock 50 mg/1 ml DMSO) 6 μl + 2994 μl DDW) |
| 3 | Compound 2 (Mw 357) 0.2 mg/Kg = 0.006 mg/0.3 ml/mouse, po (3 ml/10 mice) ((Compound 2 0.06 mg (Stock 50 mg/1 ml DMSO) 1.2 μl + 2998.8 μl DDW) |
| 4 | Compound 2 (Mw 357) 0.04 mg/Kg = 0.0012 mg/0.3 ml/mouse, po (3 ml/10 mice) ((Compound 2 0.012 mg (Stock 50 mg/1 ml DMSO) 0.24 μl + 2999.76 μl DDW) |
| 5 | Compound 2 (Mw 357) 0.008 mg/Kg = 0.00024 mg/0.3 ml/mouse, po (3 ml/10 mice) ((Compound 2 0.0024 mg (Stock 50 mg/1 ml DMSO) 0.048 (0.05) μl + 2999.95 μl DDW) |

The animals were determined on HP at: −60, 0, 60, 120, 180, 240, 300 and 360 min after treatment. The hot-plate means the temperature of 52 degrees±1.

Figure 4A:
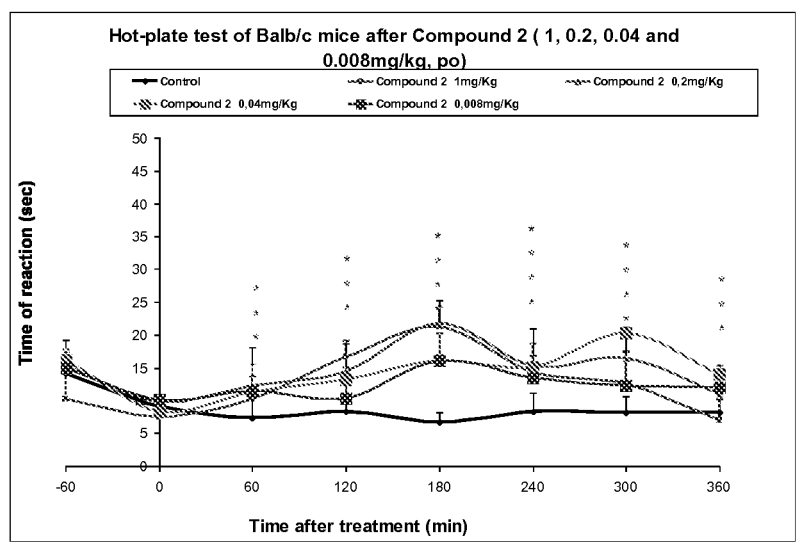
FIG. 4a provides a graph showing the results (time of reaction vs. time after treatment) of a Hot-Plate Test using Balb/c mice following administration of Compound 2 of the invention.
Figure 4B:
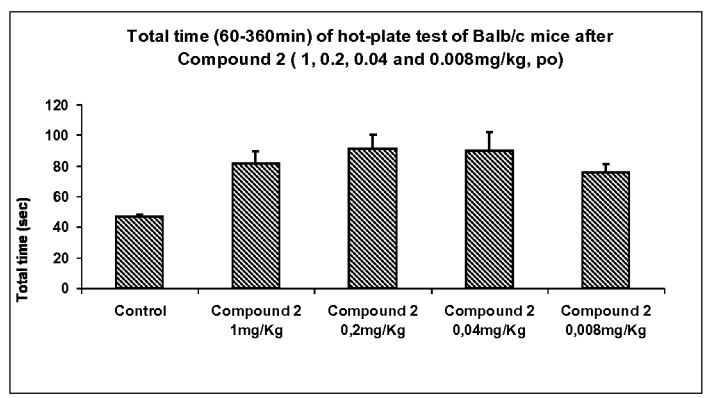
FIG. 4b provides a graph showing the results (total time vs. formulation) of a Hot-Plate Test using Balb/c mice following administration of Compound 2 of the invention.

FIGS. 4a and 4b provide data for this test.

Example 5

Nociceptin Activity Using Compound 2 and 3

Using the procedure outlined in Example 1, 40 male mice (Balb/c, 15 weeks old, not naïve), were divided in 5 groups (8 mice per group) and treated daily (0 min, p.o.) with the formulations shown in the following table.

| Formulation | Composition |
|---|---|
| 1 | Control - DDW + 0.02% DMSO 0.3 ml/mouse, po (3 ml/10 mice) (0.06 μl DMSO + 2999.94 μl DDW), n = 8. |
| 2 | Compound 2 (MW = 357) 0.01 mg/Kg = 0.0003 mg/0.3 ml/mouse, po (3 ml/10 mice) (Compound 2 0.003 mg (Stock 50 mg/1000 μl DMSO) 0.06 μl + 2999.94 μl DDW), n = 8 |
| 3 | Compound 2 0.001 mg/Kg = 0.00003 mg/0.3 ml/mouse, po (3 ml/10 mice) (Compound 2 0.0003 mg (Stock 50 mg/1000 μl DMSO) 0.006 μl + 2999.994 μl DDW), n = 8 |
| 4 | Compound 3 (MW = 343) 0.01 mg/Kg = 0.0003 mg/0.3 ml/mouse, po (3 ml/10 mice)(Compound 3 0.003 mg (Stock 50 mg/1000 μl DMSO) 0.06 μl + 2999.94 μl DDW), n = 8 |
| 5 | Compound 3 0.001 mg/Kg = 0.00003 mg/0.3 ml/mouse, po (3 ml/10 mice) (Compound 3 0.0003 mg (Stock 50 mg/1000 μl DMSO) 0.006 μl + 2999.994 μl DDW), n = 8 |

The animals were determined on HP at: −60, 0, 60, 120, 180, 240, 300 and 360 min after treatment. The hot-plate means the temperature of 52 degrees±1.

Figure 5A:
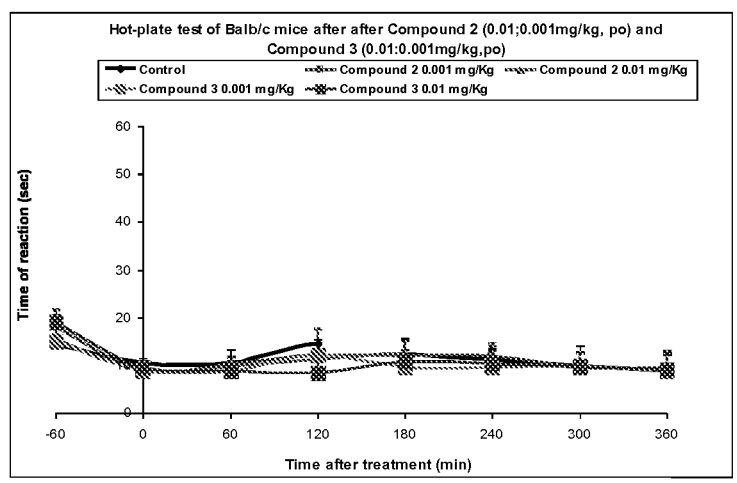
FIG. 5a provides a graph showing the results (time of reaction vs. time after treatment) of a Hot-Plate Test using Balb/c mice following administration of Compound 2 or 3 of the invention.
Figure 5B:
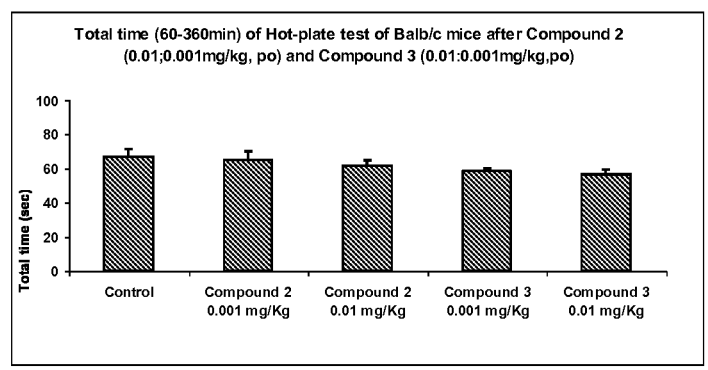
FIG. 5b provides a graph showing the results (total time vs. formulation) of a Hot-Plate Test using Balb/c mice following administration of Compound 2 or 3 of the invention.
Figure 6A:
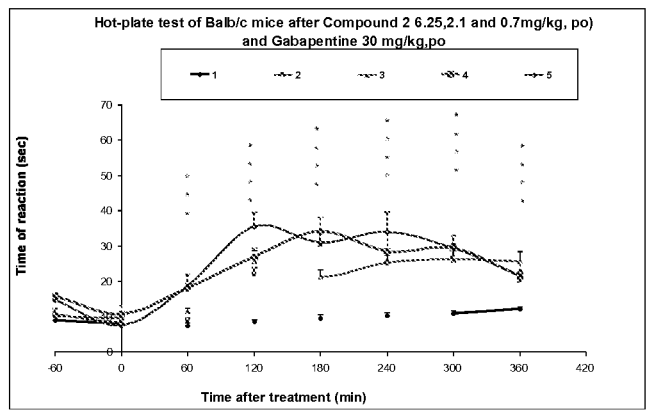
FIGS. 6a, 6b, and 6c provide graphs showing the results (time of reaction vs. time after treatment) of a Hot-Plate Test using Balb/c mice following administration of Compound 2 of the invention.
Figure 6B:
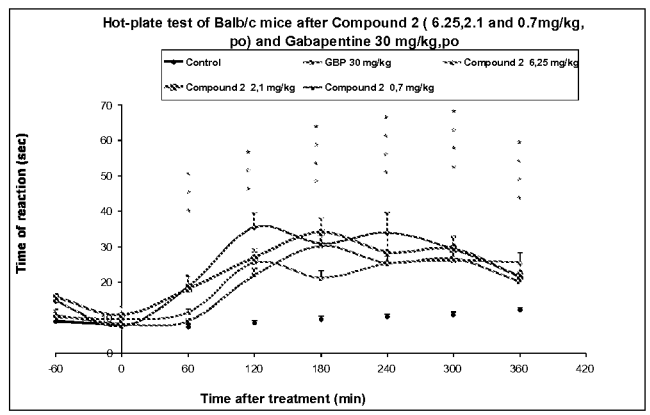
Figure 6C:
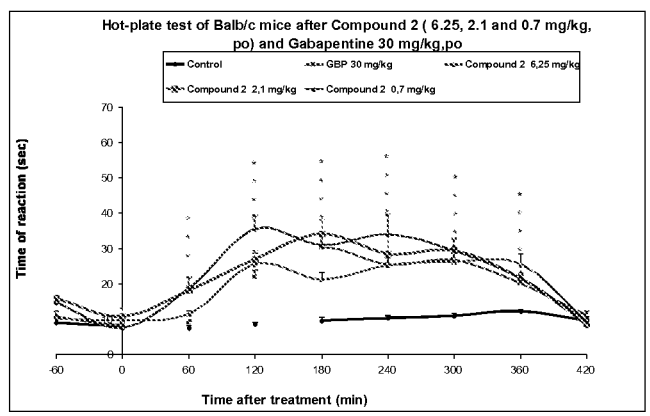
Figure 6D:
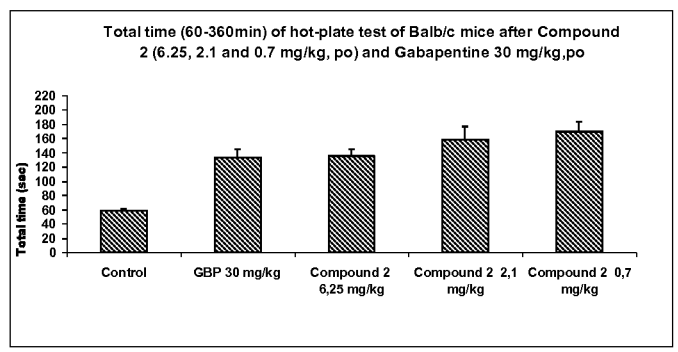
FIGS. 6d and 6e provide graphs showing the results (total time vs. formulation) of a Hot-Plate Test using Balb/c mice following administration of Compound 2 of the invention.
Figure 6E:
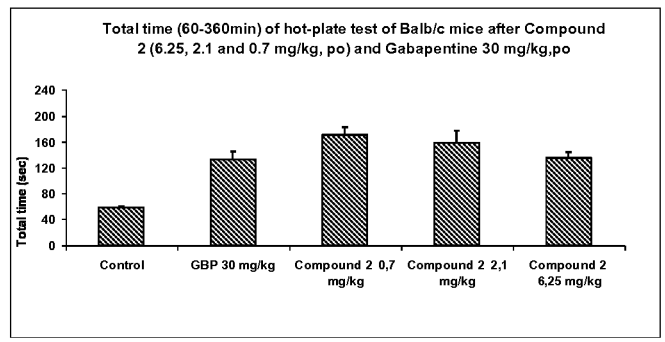
Figure 7A:
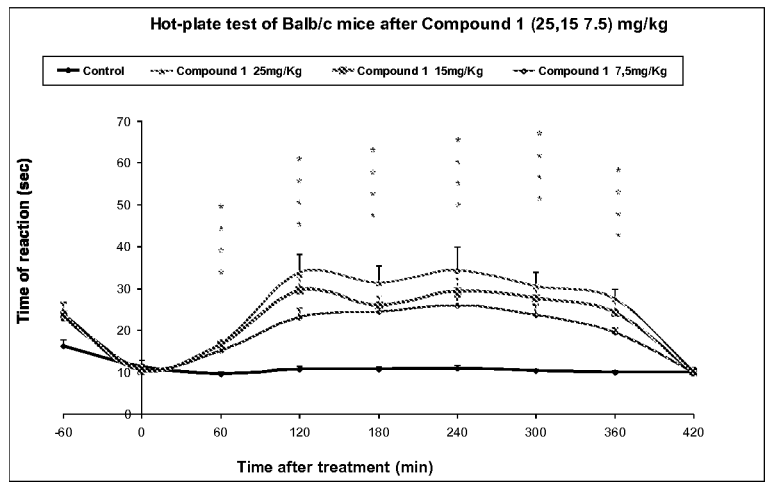
FIGS. 7a, and 7b provide graphs showing the results (time of reaction vs. time after treatment) of a Hot-Plate Test using Balb/c mice following administration of Compound 1 of the invention.
Figure 7B:
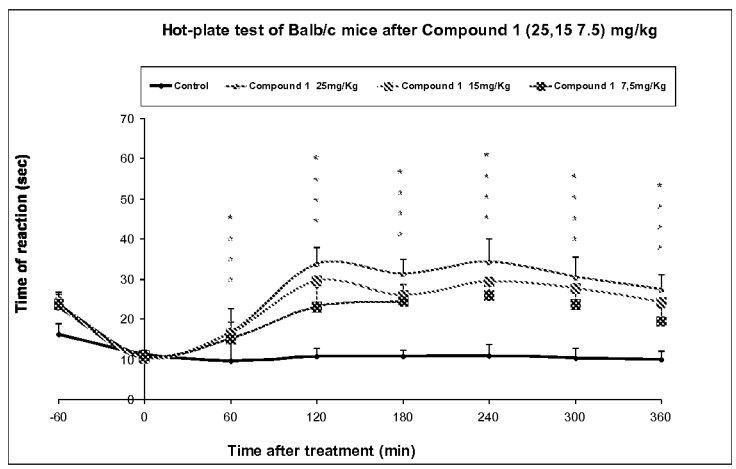
Figure 7C:
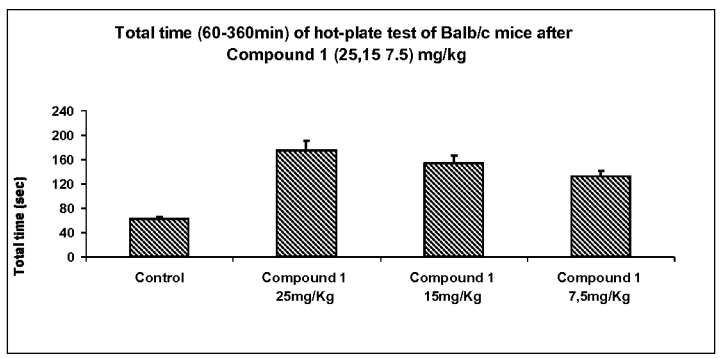
FIGS. 7c and 7d provide graphs showing the results (total time vs. formulation) of a Hot-Plate Test using Balb/c mice following administration of Compound 1 of the invention.
Figure 7D:
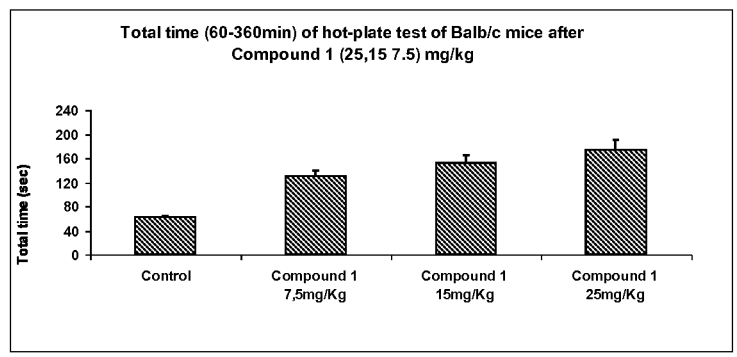

FIGS. 5a and 5b provide data for this experiment.

Example 6

Nociceptin Activity Using Compound 2

Using the procedure outlined in Example 1, 40 male mice (Balb/c, 9 weeks old, not naïve), were divided in 5 groups (8 mice per group) and treated daily (0 min, p.o.) with the formulations shown in the following table.

| Formulation | Composition |
|---|---|
| 1 | Control - DDW + 1.24% DMSO 0.25 ml/mouse, po (2.5 ml/10 mice) (31 μl DMSO + 2469 μl DDW), n = 8. |
| 2 | Compound 2 (Mw 357) 6.25 mg/Kg = 0.15625 mg/0.25 ml/mouse, po (2.5 ml/10 mice) ((Compound 2 1.5625 mg (Stock 50 mg/1 ml DMSO) 31.25 (31) μl + 2469 μl DDW) |
| 3 | Compound 2 (Mw 357) 2.083 (2.1) mg/Kg = 0.052 mg/0.25 ml/mouse, po (2.5 ml/10 mice) ((Compound 2 0.52 mg (Stock 50 mg/1 ml DMSO) 10.415 (10) μl + 2490 μl DDW) |
| 4 | Compound 2 (Mw 357) 0.694 (0.7) mg/Kg = 0.01735 mg/0.25 ml/mouse, po (2.5 ml/10 mice) ((Compound 2 0.1735 mg (Stock 50 mg/1 ml DMSO) 3.47 (3) μl + 2497 μl DDW) |
| 5 | Gabapentine (GBP) 30 mg/Kg = 7.5 mg/0.25 ml/mouse, po (2.5 ml/10 mice) (GBP 7.5 mg + 2500 μl DDW) |

The animals were determined on HP at: −60, 0, 60, 120, 180, 240, 300 and 360 min, and 24 h after treatment. The hot-plate means the temperature of 52 degrees±1

FIGS. 6a-e provide the data from this test.

Example 7

Nociceptin Activity Using Compound 1

Using the procedure outlined in Example 1, 40 male mice (Balb/c, 12 weeks old, naïve), were divided in 5 groups (8 mice per group) and treated daily (0 min, p.o.) with the formulations shown in the following table.

| Formulation | Composition |
|---|---|
| 1 | Control - DDW + 5% DMSO 0.25 ml/mouse, po (2.5 ml/10 mice) (125 μl DMSO + 2375 μl DDW), n = 8. |
| 2 | Compound 1 25 mg/Kg = 0.625 mg/0.25 ml/mouse, po (2.5 ml/10 mice) (Compound 1 1.5625 mg (Stock 30 mg/0.6 ml DMSO) 32 μl + 2468 μl DDW) |
| 3 | Compound 1 (Mw 415) eqM 25 mg/Kg (15 mg/kg) = 3.75 mg/0.25 ml/mouse, po (2.5 ml/10 mice) (Compound 1 3.75 mg (Stock 30 mg/0.6 ml DMSO) 75 μl + 2425 μl DDW) |
| 4 | Compound 1 (Mw 415) eqM 12.5 mg/Kg (7.5 mg/kg) = 1.875 mg/0.25 ml/mouse, po (2.5 ml/10 mice)(Compound 1 1.875 mg (Stock 30 mg/0.6 ml DMSO) 37.5 (38) μl + 2462 μl DDW) |

The animals were determined on HP at: −60, 0, 60, 120, 180, 240, 300 and 360 min, and 24 h. The hot-plate means the temperature of 52 degrees±1.

FIGS. 7a-d provide data for this experiment.

Example 8

Nociceptin Activity Using Compound 3

Using the procedure outlined in Example 1, 37 male mice (Balb/c, 16 weeks old, not naïve), were divided in 5 groups and treated daily (0 min, p.o.) with the formulations shown in the following table.

| Formulation | Composition |
| --- | --- |
| 1 | Control - DDW + 1.2% DMSO 0.3 ml/mouse, po (3 ml/10 mice) (36 μl DMSO + 2964 μl DDW), n = 7. |
| 2 | Compound 3 (MW = 343) 0.06 mg/Kg = 0.0018 mg/0.3 ml/mouse, po (3 ml/10 mice) (Compound 3 0.018 mg (Stock 4.6 mg/92 μl DMSO) 0.36 μl + 2999.64 μl DDW), n = 7 |
| 3 | Compound 3 0.6 mg/Kg = 0.018 mg/0.3 ml/mouse, po (3 ml/10 mice) (Compound 3 0.18 mg (Stock 4.6 mg/92 μl DMSO) 3.6 μl + 2996.4 μl DDW), n = 7 |
| 4 | Compound 3 6 mg/Kg = 0.18 mg/0.3 ml/mouse, po (3 ml/10 mice) (Compound 3 1.8 mg (Stock 4.6 mg/92 μl DMSO) 36 μl + 2964 μl DDW), n = 8 |
| 5 | Diclofenac 50 mg/Kg = 1.25 mg/0.3 ml/mouse, po (3 ml/10 mice) Diclofenac 14.4 mg + 0.25 μl DMSO + 2999.75 μl DDW), n = 8 |

The animals were determined on HP at: −60, 0, 60, 120, 180, 240, 300 and 360 min after treatment. The hot-plate means the temperature of 52 degrees±1.

Figure 8A:
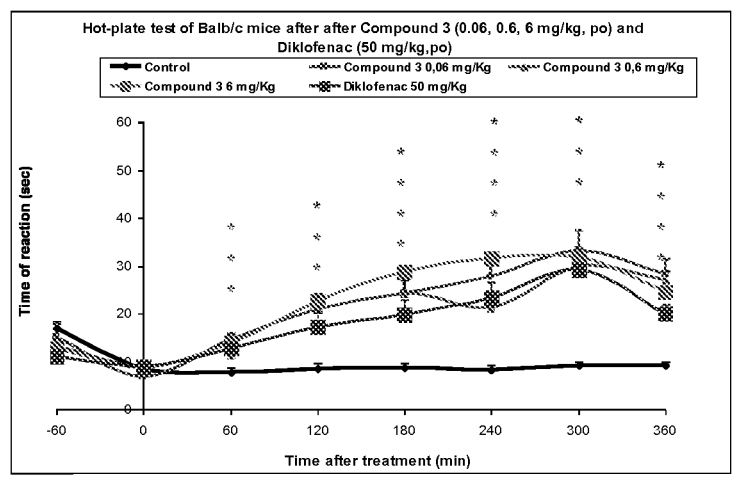
FIG. 8a provides a graph showing the results (time of reaction vs. time after treatment) of a Hot-Plate Test using Balb/c mice following administration of Compound 3 of the invention.
Figure 8B:
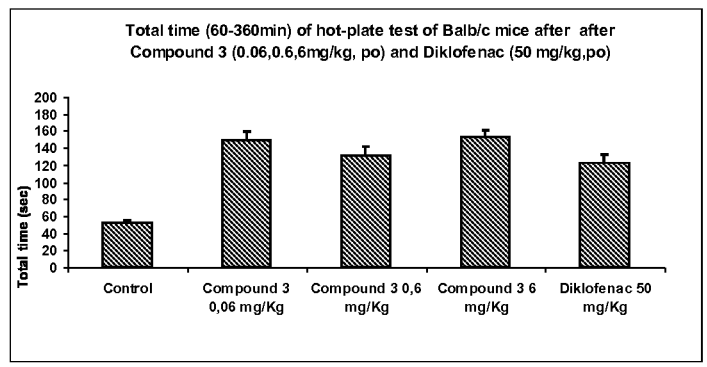
FIG. 8b provides a graph showing the results (total time vs. formulation) of a Hot-Plate Test using Balb/c mice following administration of Compound 3 of the invention.
Figure 9A:
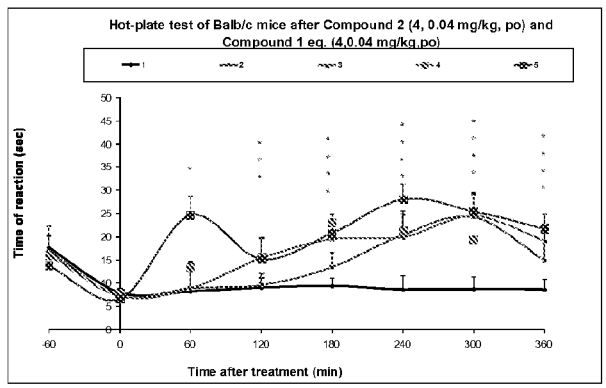
FIGS. 9a, and 9b provide graphs showing the results (time of reaction vs. time after treatment) of a Hot-Plate Test using Balb/c mice following administration of Compound 1 or 2 of the invention.
Figure 9B:
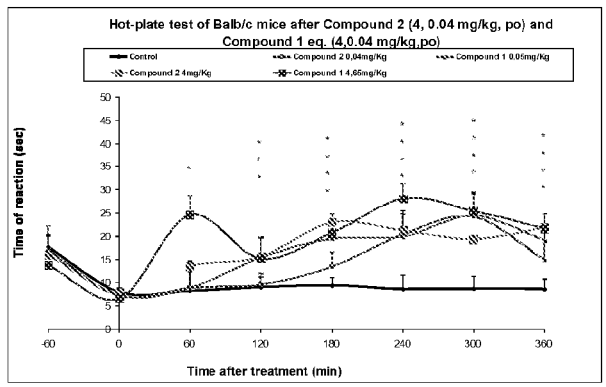
Figure 9C:
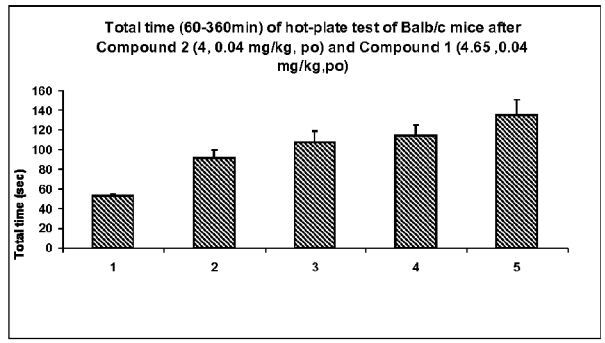
FIGS. 9c, 9d, 9e provide graphs showing the results (total time vs. formulation) of a Hot-Plate Test using Balb/c mice following administration of Compound 1 or 2 of the invention.
Figure 9D:
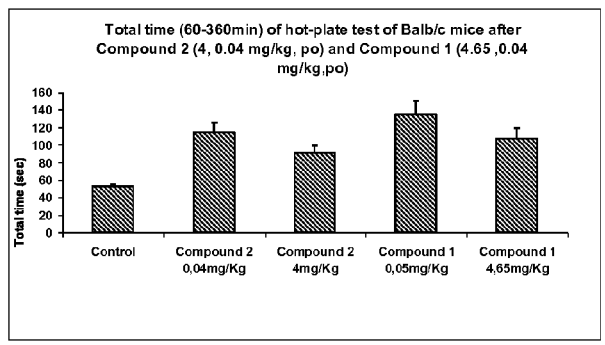
Figure 9E:
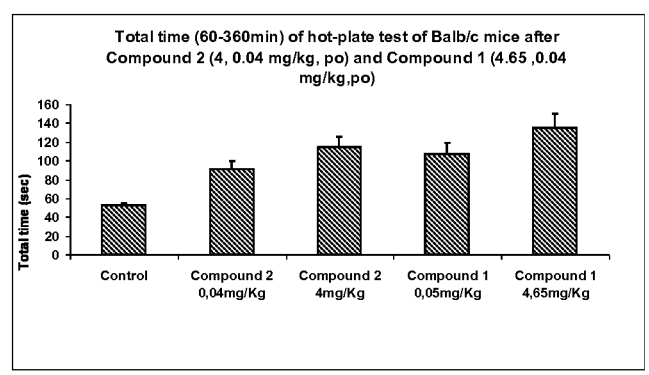

FIGS. 8a and 8b provide data for this experiment.

Example 9

Nociceptin Activity Using Compounds 1 and 2

Using the procedure outlined in Example 1, 40 male mice (Balb/c, 13 weeks old, not naïve), were divided in 5 groups and treated daily (0 min, p.o.) with the formulations shown in the following table.

| Formulation | Composition |
| --- | --- |
| 1 | Control - DDW + 0.8% DMSO 0.3 ml/mouse, po (3 ml/10 mice) (24 μl DMSO + 2976 μl DDW), n = 8. |
| 2 | Compound 2 (Mw 357) 4 mg/Kg = 0.12 mg/0.3 ml/mouse, po (3 ml/10 mice) ((Compound 2 1.2 mg (Stock 50 mg/1 ml DMSO) 24 μl + 2976 μl DDW) |
| 3 | Compound 2 (Mw 357) 0.04 mg/Kg = 0.0012 mg/0.3 ml/mouse, po (3 ml/10 mice) ((Compound 2 0.012 mg (Stock 50 mg/1 ml DMSO) 0.24 μl + 2999.76 μl DDW) |
| 4 | Compound 1 (Mw 415) eq.4 (4.65) mg/Kg = 0.14 mg/0.3 ml/mouse, po (3 ml/10 mice) ((Compound 1 1.395 mg (Stock 30 mg/0.6 ml DMSO) 27.9 (28) μl + 2972 μl DDW) |
| 5 | Compound 1 (Mw 415) eq.0.04 (0.05) mg/Kg = 0.0014 mg/0.3 ml/mouse, po (3 ml/10 mice) ((Compound 1 0.014 mg (Stock 60 mg/0.6 ml DMSO) 0.279 (0.28) μl + 2999.72 μl DDW) |

The animals were determined on HP at: −60, 0, 60, 120, 180, 240, 300 and 360 min after treatment. The hot-plate means the temperature of 52 degrees±1.

FIGS. 9a-e provide data for this experiment.

Example 10

Nociceptin Activity Using Compounds 1 and 2

Using the procedure outlined in Example 1, 40 male mice (Balb/c, 13 weeks old, not naïve), were divided in 5 groups and treated daily (0 min, p.o.) with the formulations shown in the following table.

| Formulation | Composition |
|---|---|
| 1 | Control - DDW + 0.04% DMSO 0.3 ml/mouse, po (3 ml/10 mice) (1.2 μl DMSO + 2998.8 μl DDW), n = 8. |
| 2 | Compound 1 0.125 mg/Kg = 0.00375 mg/0.3 ml/mouse, po (3 ml/10 mice) (Compound 1 0.0375 mg (Stock 60 mg/1.2 ml DMSO) 0.75 μl + 2999.25 μl DDW), n = 8 |
| 3 | Compound 2 0.1 mg/Kg = 0.003 mg/0.3 ml/mouse, po (3 ml/10 mice) (Compound 2 0.03 mg (Stock 60 mg/1.2 ml DMSO) 0.6 μl + 2999.4 μl DDW), n = 8 |
| 4 | Diclofenac 50 mg/Kg = 1.25 mg/0.3 ml/mouse, po (3 ml/10 mice) Diclofenac 12.5 mg + 0.25 μl DMSO + 2999.75 μl DDW), n = 8 |

The animals were determined on HP at: −60, 0, 60, 120, 180, 240, 300 and 360 min after treatment. The hot-plate means the temperature of 52 degrees±1.

Figure 10A:
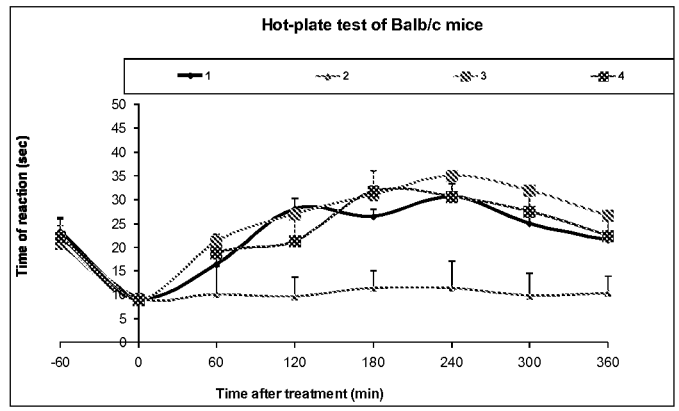
FIGS. 10a and 10b provide graphs showing the results (time of reaction vs. time after treatment) of a Hot-Plate Test using Balb/c mice following administration of Compound 1 or 2 of the invention.
Figure 10B:
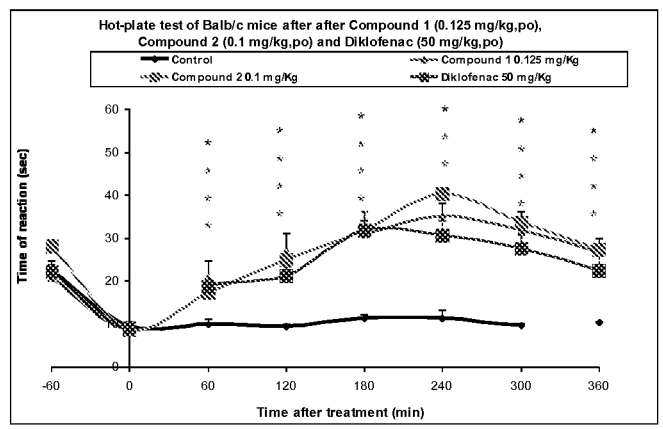
Figure 10C:
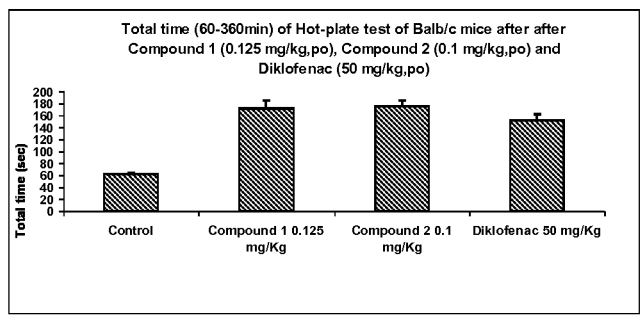
FIG. 10c provides a graph showing the results (total time vs. formulation) of a Hot-Plate Test using Balb/c mice following administration of Compound 1 or 2 of the invention.

FIGS. 10a, 10b, and 10c provide data for this experiment.

Example 11

Edema Test

Male SD rats (9 weeks old, naïve), were divided into 5 groups (6 mice in each group) and treated (−120 min, p.o.) with the formulations shown in the following table.

| Formulation | Composition |
|---|---|
| 1 | Control - DDW + 10% DMSO 0.3 ml/rat, po (2.4 ml/8 rats) (241 μl DMSO + 2159 μl DDW) |
| 2 | Compound 2, 1 mg/Kg = 0.3 mg/0.3 ml/rat, po (2.4 ml/8 rats) (Compound 2, 2.4 (Stock 21.5 mg/0.43 ml DMSO) 32 μl + 2352 μl DDW) |
| 3 | Compound 2, 5 mg/Kg = 1.5 mg/0.3 ml/rat, po (2.4 ml/8 rats) (Compound 2, 12 mg (Stock 21.5 mg/0.43 ml DMSO) 241 μl + 2159 μl DDW) |
| 4 | Compound 3 1 mg/Kg = 0.3 mg/0.3 ml/rat, po (2.4 ml/8 rats) (Compound 3 2.4 mg (Stock 19.1 mg/0.382 ml DMSO) 32 μl + 2352 μl DDW) |
| 5 | Compound 3 5 mg/Kg = 1.5 mg/0.3 ml/rat, po (2.4 ml/8 rats) (Compound 3, 12 mg (Stock 19.1 mg/0.382 ml DMSO) 241 μl + 2159 μl DDW) |

Figure 11:
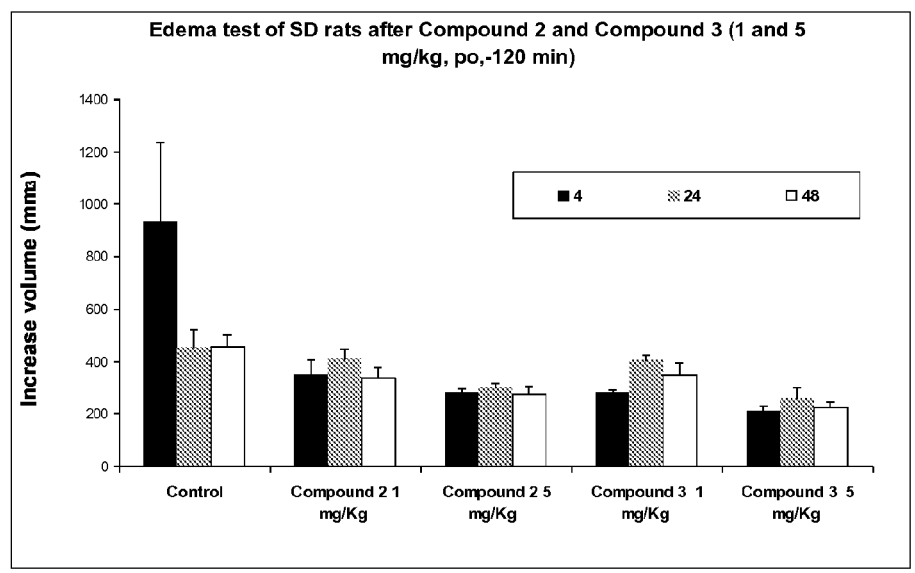
FIG. 11 provides a graph showing the results (increased volume vs. formulation of an edema test of SD rats following administration of Compound 2 or 3 of the invention.

FIG. 11 provides data from this test.

Example 12

Formalin Test

Formalin test. The method used was similar to that described by Hunscaar and Hole (1987) "The formalin test in mice: dissociation between inflammatory and non-inflammatory pain," Pain 30, pp. 103-104.

Five animals are used in each group and two to three hours after oral administration of the conjugates, 40 μl or 20 μl (rats or mice, respectively) of a 1% formalin (in 0.9% saline) solution is injected subcutaneously into the dorsal surface hind paw. The formalin induced typical flinching behaviour of the injected paw which was counted. The animals were returned to a glass chamber and the total time spent by the animal licking or biting the injected paw was measured. Formalin induced pain behaviour is biphasic. The duration of paw licking was determined during the following two time periods: 0-5 min (first-neurogenic phase) and 20-30 min (second-inflammatory phase) after formalin injection.

Part a. Male mice (Balb/c mice, 27 weeks old, not naïve), were divided in 4 groups (5 mice per group) and treated (0 min, i.p.) with the following formulations, respectively:

| Formulation | Composition |
|---|---|
| 1a | Control - (0.2 ml DMSO + 3.52 saline) i.p. 0.3 ml/mouse. n = 5. |
| 2a | Compound 2, 0.2 mg/kg = 0.006 mg/0.3 ml/mouse, 6 mice/0.036 mg/1.8 ml = |

-continued

| Formulation | Composition |
|---|---|
| | (0.72 μl (2 mg compound 2 + 40 μl DMSO) + 1799.28 μl DDW) n = 5. |
| 3a | Compound 2, 1 mg/kg = 0.03 mg/0.3 ml/mouse, 6 mice/0.18 mg/1.8 ml = (3.6 μl (2 mg compound 2 + 40 μl DMSO) + 1796.4 μl DDW) n = 5. |
| 4a | Compound 2, 2.5 mg/kg = 0.15 mg/0.3 ml/mouse, 6 mice/0.9 mg/1.8 ml = (9 μl (2 mg stock compound 2 + 40 μl DMSO) + 1782 μl DDW) n = 5. |

Part b. Male mice (Balb/c mice, 27 weeks old, not naïve), were divided in 4 groups (5 mice in groups) and treated (0 min, i.p.) with the following formulations, respectively:

| Formulation | Composition |
|---|---|
| 1b | Control - (0.2 ml DMSO + 3.52 saline) i.p. 0.3 ml/mouse. n = 5. |
| 2b | Compound 2 0.2 mg/kg = 0.006 mg/0.3 ml/mouse, 6 mice/0.036 mg/1.8 ml = (0.72 μl (1.3 mg compound 2 + 26 μl DMSO) + 1799.28 μl DDW) n = 5. |
| 3b | Compound 2 1 mg/kg = 0.03 mg/0.3 ml/mouse, 6 mice/0.18 mg/1.8 ml = (3.6 μl (1.3 mg compound 2 + 26 μl DMSO) + 1796.4 μl DDW) n = 5. |
| 4b | Compound 2 2.5 mg/kg = 0.15 mg/0.3 ml/mouse, 6 mice/0.9 mg/1.8 ml = (9 μl (1.3 mg compound 2 + 26 μl DMSO) + 1782 μl DDW) n = 5. |

TABLE 1a

Data from Part a.
Formalin 1% (50 μl) intraplantar route in the right hind paw (3 h after the treatment)

| # mouse | weight | treatment | Formalin | 5 min | inflam. | 10 min |
|---|---|---|---|---|---|---|
| 1 | | 08:20 | 11:20 | | 11:40 | |
| 2 | | 08:30 | 11:30 | | 11:50 | |
| 3 | | 08:40 | 11:40 | | 12:00 | |
| 4 | | 08:50 | 11:50 | | 12:10 | |
| 5 | | 09:00 | 12:00 | | 12:20 | |
| 6 | | 09:10 | 12:10 | | 12:30 | |
| 7 | | 09:20 | 12:20 | | 12:40 | |
| 8 | | 09:30 | 12:30 | | 12:50 | |
| 9 | | 09:40 | 12:40 | | 13:00 | |
| 10 | | 09:50 | 12:50 | | 13:10 | |
| 11 | | 10:50 | 13:50 | | 14:10 | |
| 12 | | 11:00 | 14:00 | | 14:20 | |
| 13 | | 11:10 | 14:10 | | 14:30 | |
| 14 | | 11:20 | 14:20 | | 14:40 | |
| 15 | | 11:30 | 14:30 | | 14:50 | |
| 16 | | 11:40 | 14:40 | | 15:00 | |
| 17 | | 11:50 | 14:50 | | 15:10 | |
| 18 | | 12:00 | 15:00 | | 15:20 | |
| 19 | | 12:10 | 15:10 | | 15:30 | |
| 20 | | 12:20 | 15:20 | | 15:40 | |

TABLE 1b

Data from Part b.
Formalin 1% (50 μl) intraplantar route in the right hind paw (4 h after the treatment)

| # mouse | weight | treatment | Formalin | 5 min | inflam. | 10 min |
|---|---|---|---|---|---|---|
| 1 | | 06:30 | 10:30 | | 10:50 | |
| 2 | | 06:40 | 10:40 | | 11:00 | |
| 3 | | 06:50 | 10:50 | | 11:10 | |
| 4 | | 07:00 | 11:00 | | 11:20 | |
| 5 | | 07:10 | 11:10 | | 11:30 | |
| 6 | | 07:20 | 11:20 | | 11:40 | |
| 7 | | 07:30 | 11:30 | | 11:50 | |
| 8 | | 07:40 | 11:40 | | 12:00 | |
| 9 | | 07:50 | 11:50 | | 12:10 | |
| 10 | | 08:00 | 12:00 | | 12:20 | |
| 11 | | 08:10 | 12:10 | | 12:30 | |
| 12 | | 08:20 | 12:20 | | 12:40 | |
| 13 | | 08:30 | 12:30 | | 12:50 | |
| 14 | | 08:40 | 12:40 | | 13:00 | |
| 15 | | 08:50 | 12:50 | | 13:10 | |
| 16 | | 09:00 | 13:00 | | 13:20 | |
| 17 | | 09:10 | 13:10 | | 13:30 | |
| 18 | | 09:20 | 13:20 | | 13:40 | |
| 19 | | 09:30 | 13:30 | | 13:50 | |
| 20 | | 09:40 | 13:40 | | 14:00 | |

Figure 12A:
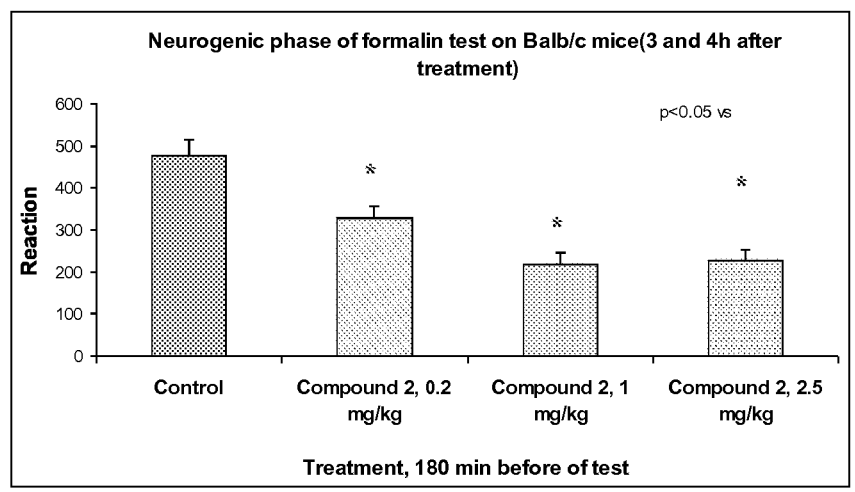
FIGS. 12a-12e provide graphs showing the results (reaction vs. formulation) of a formalin test on Balb/c mice following administration of Compound 1 or 2 of the invention.
Figure 12B:
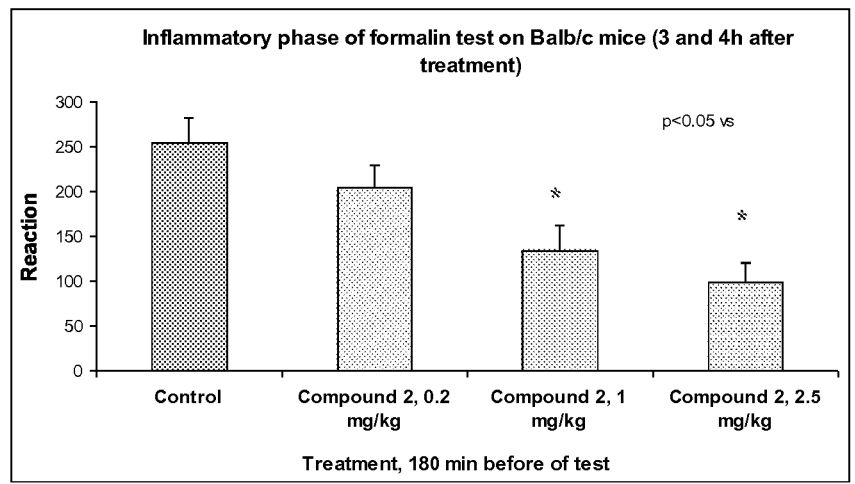
Figure 12C:
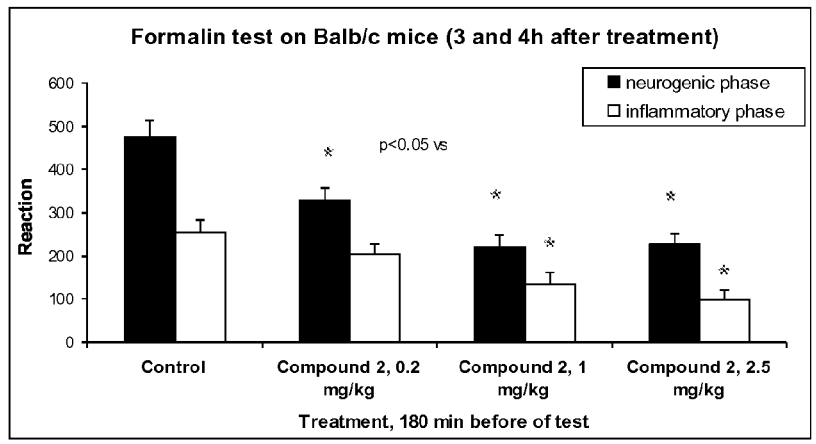
Figure 12D:
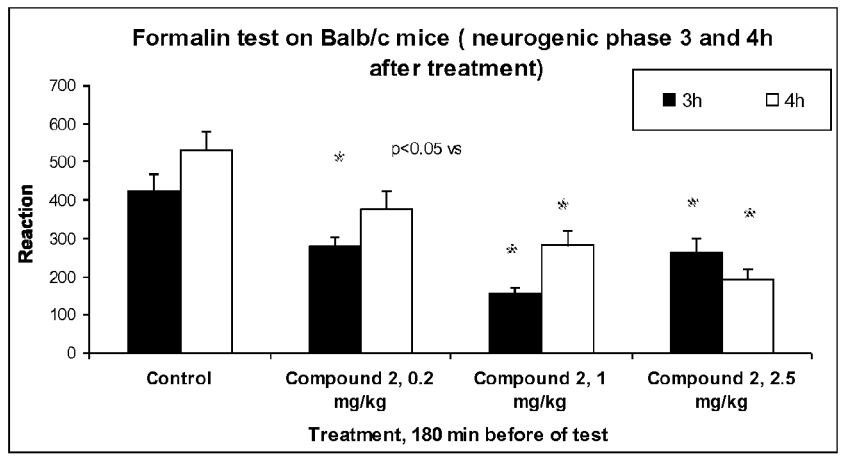
Figure 12E:
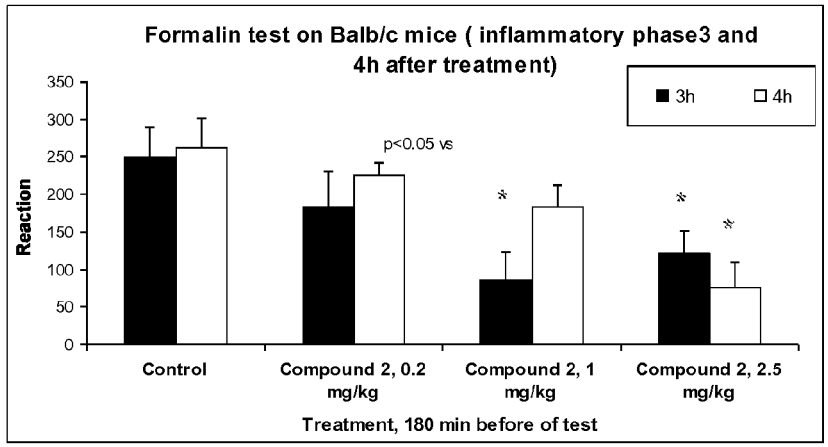

Results from these tests are plotted in FIGS. 12a and 12b respectively. FIGS. 12c, 12d, and 12e provide further data based on measurement time. These data further confirm the anti-inflammatory properties of Compound 2.

The invention claimed is:

1. A method for treating nociceptive pain selected from somatic, visceral, and myofascial or edema in a human or non-human animal patient in need thereof, which method comprises administering to said patient a therapeutically effective amount of at least one compound represented by formula I:

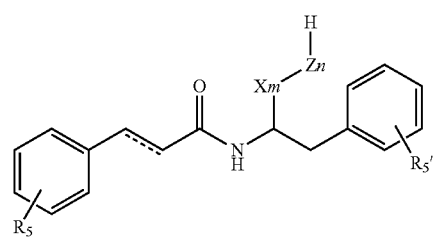

(I)

wherein:

---- represents a single or a double bond;
$R_5$ and $R_5'$ are independently —H, —OH or —OR$_6$, wherein R$_6$ is a linear or branched $C_1$-$C_4$ alkyl;

X is —CH$_2$O—;
Z is —CH$_2$CH$_2$O—, —CH(CH$_3$)CH$_2$O— or —CH$_2$CH(CH$_3$)O—;
m is 1; and
n is an integer of 1, 2, 3, 4, or 5;
or a pharmaceutically acceptable salt, prodrug, metabolite, or hydrate thereof.

2. The method as claimed in claim 1 for the treatment of acute or chronic nociceptive pain.

3. The method as claimed in claim 1, wherein the compound is represented by formula III:

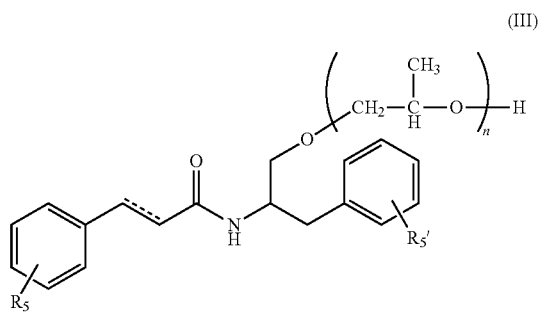

(III)

or a pharmaceutically acceptable salt, prodrug, metabolite, or hydrate thereof.

4. The method as claimed in claim 1, wherein R$_5$ is H or OH.

5. The method as claimed in claim 1, wherein R$_5$' is H or OH.

6. The method as claimed in claim 3, wherein n is 1 or 2.

7. The method as claimed in claim 1, wherein the compound is represented by formula IV, V, VI or VII:

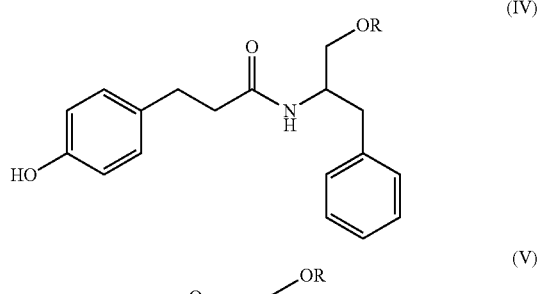

(IV)

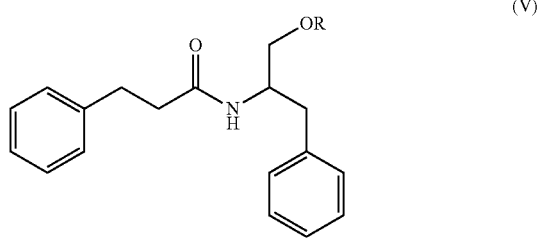

(V)

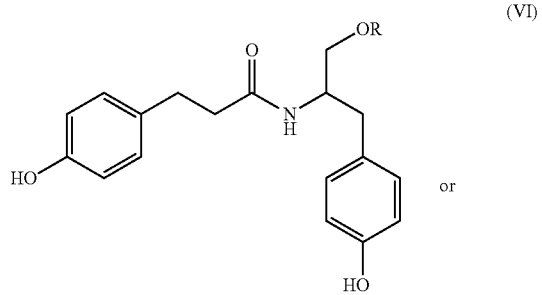

(VI)

or

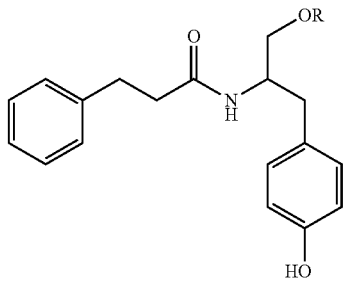

(VII)

or a pharmaceutically acceptable salt, prodrug, metabolite, or hydrate thereof,
wherein R is a polyalkylene glycol polymer having n units, wherein n is an integer of 1, 2, 3, 4, or 5.

8. The method as claimed in claim 1, wherein the compound is administered as a pharmaceutical composition comprising a therapeutically effective amount of one or more of the compounds represented by formula I together with one or more pharmaceutically acceptable excipients.

9. The method as claimed in claim 1 for the treatment of somatic pain or visceral pain, wherein said somatic pain originates from tendons, bones, blood vessels or nerves.

10. The method as claimed in claim 9 for the treatment of phantom limb pain.

11. The method as claimed in claim 1 for the treatment of edema.

12. The method as claimed in claim 1, wherein the compound is selected from

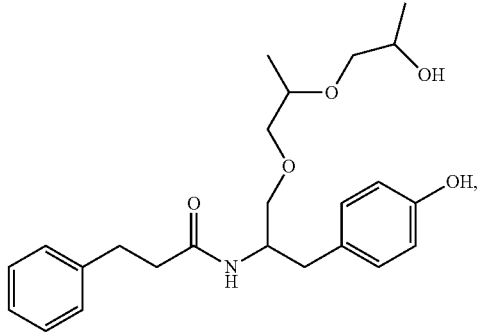

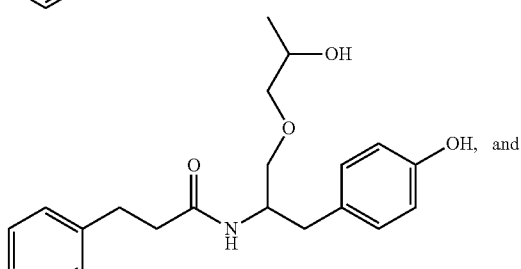

and

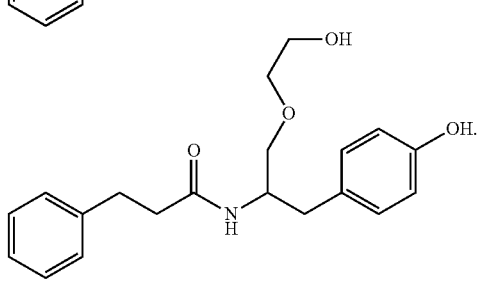

13. The method as claimed in claim 9 for the treatment of headache.

14. A method for treating somatic pain, visceral pain, myofascial pain, or edema in a human patient in need thereof, which method comprises administering to said patient a therapeutically effective amount of the compound:

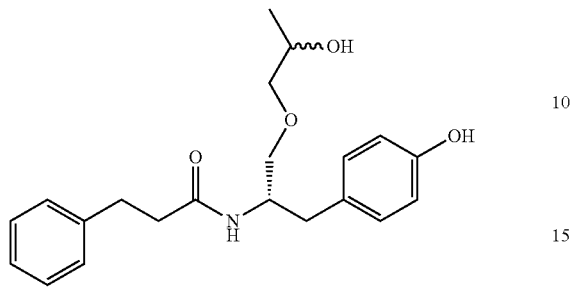

or a pharmaceutically acceptable salt thereof.

15. The method as claimed in claim 14 for the treatment of somatic pain, wherein said somatic pain originates from tendons, bones, blood vessels or nerves.

16. The method as claimed in claim 15 for the treatment of headache.

17. The method as claimed in claim 14 for the treatment of visceral pain.

18. The method as claimed in claim 14 for the treatment of phantom limb pain.

19. The method as claimed in claim 14 for the treatment of myofascial pain.

20. The method as claimed in claim 10 for the treatment of edema.

* * * * *